US011132798B2

(12) United States Patent
Yan et al.

(10) Patent No.: US 11,132,798 B2
(45) Date of Patent: Sep. 28, 2021

(54) TUMOR TRACKING METHOD AND DEVICE, AND STORAGE MEDIUM

(71) Applicants: OUR UNITED CORPORATION, Xi'an (CN); SHENZHEN OUR NEW MEDICAL TECHNOLOGIES DEVELOPMENT CO., LTD., Shenzhen (CN)

(72) Inventors: Hao Yan, Xi'an (CN); Jinsheng Li, Xi'an (CN); Jiuliang Li, Xi'an (CN); Haifeng Liu, Xi'an (CN)

(73) Assignees: OUR UNITED CORPORATION, Xi'an (CN); SHENZHEN OUR NEW MEDICAL TECHNOLOGIES DEVELOPMENT CO., LTD., Shenzhen (CN)

( * ) Notice: Subject to any disclaimer, the term of this patent is extended or adjusted under 35 U.S.C. 154(b) by 0 days.

(21) Appl. No.: 16/634,500

(22) PCT Filed: Jul. 28, 2017

(86) PCT No.: PCT/CN2017/095041
§ 371 (c)(1),
(2) Date: Jan. 27, 2020

(87) PCT Pub. No.: WO2019/019188
PCT Pub. Date: Jan. 31, 2019

(65) Prior Publication Data
US 2020/0234443 A1     Jul. 23, 2020

(51) Int. Cl.
*G06K 9/00* (2006.01)
*G06T 7/00* (2017.01)
*A61N 5/10* (2006.01)
(52) U.S. Cl.
CPC ............ *G06T 7/0014* (2013.01); *A61N 5/103* (2013.01); *G06T 2207/10016* (2013.01);
(Continued)

(58) Field of Classification Search
None
See application file for complete search history.

(56) References Cited

U.S. PATENT DOCUMENTS

| 9,271,692 B2 | 3/2016 | Mostafavi |
| 9,468,395 B2 | 10/2016 | Fontius |

(Continued)

FOREIGN PATENT DOCUMENTS

| CN | 1672651 A | 9/2005 |
| CN | 1853737 A | 11/2006 |

(Continued)

OTHER PUBLICATIONS

International Search Report; PCT/CN2017/059041; dated Apr. 28, 2018; 5 pages.

(Continued)

*Primary Examiner* — Atiba O Fitzpatrick
(74) *Attorney, Agent, or Firm* — Knobbe Martens Olson & Bear LLP

(57) ABSTRACT

Provided is a tumor tracking method including: acquiring a detection image when a first ray source is located at a first detection point; determining, from a first reference image sequence in a preset image library, a first reference image corresponding to the detection image; acquiring, from a second reference image sequence corresponding to the first reference image sequence in the preset image library, a second reference image determined at the same time point as the first reference image; and determining a position of a tumor relative to a second ray source according to the second reference image.

20 Claims, 14 Drawing Sheets

(52) U.S. Cl.
CPC .............. *G06T 2207/10028* (2013.01); *G06T 2207/10076* (2013.01); *G06T 2207/20081* (2013.01); *G06T 2207/30096* (2013.01)

(56) References Cited

U.S. PATENT DOCUMENTS

| | | | | |
|---|---|---|---|---|
| 2006/0163495 | A1* | 7/2006 | Hiramoto | A61N 5/1049 250/492.3 |
| 2007/0237290 | A1* | 10/2007 | Mostafavi | A61B 6/032 378/21 |
| 2010/0067660 | A1* | 3/2010 | Maurer, Jr. | A61B 6/541 378/95 |
| 2010/0067739 | A1* | 3/2010 | Mostafavi | G06T 7/285 382/103 |
| 2014/0050297 | A1* | 2/2014 | Mostafavi | A61B 6/486 378/8 |
| 2016/0023019 | A1* | 1/2016 | Filiberti | A61N 5/10 600/1 |
| 2016/0174921 | A1* | 6/2016 | Wikler | A61B 6/032 378/19 |
| 2017/0361128 | A1* | 12/2017 | Lachaine | G01R 33/4808 |

FOREIGN PATENT DOCUMENTS

| | | |
|---|---|---|
| CN | 101559260 A | 10/2009 |
| CN | 101623198 A | 1/2010 |
| CN | 102341044 A | 2/2012 |
| CN | 103430213 A | 12/2013 |
| CN | 106563210 A | 4/2017 |
| CN | 106714905 A | 5/2017 |
| EP | 1977788 A3 | 10/2009 |

OTHER PUBLICATIONS

First Office Action of corresponding Chinese Patent Application No. 201780042615.2—20 pages (dated Jun. 1, 2020).

* cited by examiner

TUMOR TRACKING METHOD AND DEVICE, AND STORAGE MEDIUM

CROSS-REFERENCE TO RELATED APPLICATION

This application is a 371 application of PCT international patent application No.: PCT/CN2017/095041 filed on Jul. 28, 2017.

TECHNICAL FIELD

The present disclosure relates to the field of object positioning technologies, and more particularly, to a tumor tracking method and device, and a storage medium.

BACKGROUND

Radiation therapy (or radiotherapy) is a local treatment method of tumors by using radioactive rays (such as x-rays, β-rays and γ-rays). One of the key technologies in radiation therapy lies in the accurate positioning of the tumors. Generally, for a movable tumor, it would be a necessity to track the tumor to achieve the accurate positioning. For example, when conducting a radiation therapy on lung tumor (i.e., the tumor growing in a lung of a patient), due to the movement of the tumor along with the breathing of the patient, it is necessary to track the tumor in the process.

In the related art, a first tumor tracking method uses external surrogate signals associated with breathing. By monitoring the signal, the movement of a tumor can be predicted. The external surrogate signal may include the up and down movement of a marker on the body surface of a patient, the increase or decrease of the amount of gas that a patient breathes, or a change in the abdominal pressure of a patient. A second tumor tracking method employs two projection equipment that are at an angle with each other to directly perform a fluoroscopy imaging on the tumor area. Each of the projection equipment includes a ray source and a detector. In this method, through the 2D location of a tumor in two X-ray projections that are at an angle with each other, the 3D spatial position of the tumor can be inversely calculated. At present, the above two types of the methods are generally combined in the tracking of tumor movement.

In the process of implementing the present disclosure, the inventor finds that at least the following problems exist in the related art.

The main disadvantage of the first method (monitoring the external surrogate signals associated with breathing) is that the signal cannot accurately characterize the movement of the tumor, which results in a high uncertainty. The main disadvantage of the second method (performing fluoroscopy imaging on the tumor) is that due to the influence of X-rays dose, this method can only be used at intervals (for example, with an interval of 10 seconds). Currently, it is generally employed to calibrate the phase shift present in the first method, after a certain time interval. In addition, both methods require additional hardware equipment. The current X-ray fluoroscopy-based method generally requires two mutually-angled projections, or a single projection at a constant angle. However, the actual equipment in most practice uses a flat panel rotated along with a rack to generate a single projection with varying angles. Thus, in such cases, the current methods are not suitable.

SUMMARY

To solve the problem of high cost in tumor tracking, embodiments of the present disclosure provide a tumor tracking method and device, and a storage medium. The technical solutions are as follows.

In a first aspect, there is provided a tumor tracking method applied to radiation therapy equipment. The radiation therapy equipment includes a first ray source, a second ray source and a detector. When the first ray source is located at a first detection point, the second ray source is located at a second detection point. The method includes:

acquiring a detection image when the first ray source is located at the first detection point, wherein the detection image is an image determined when a radioactive ray, emitted by the first ray source at the first detection point toward a tumor area, is received by the detector;

determining, from a first reference image sequence in a preset image library, a first reference image corresponding to the detection image, wherein the preset image library comprises the first reference image sequence and a second reference image sequence, the first reference image sequence is a reference image sequence determined based on an optical signal sent from a position of a first collection point toward the tumor area, the second reference image sequence is a reference image sequence determined based on an optical signal sent from a position of a second collection point toward the tumor area, the first detection point and the first collection point are at the same position relative to the tumor area, the second detection point and the second collection point are at the same position relative to the tumor area, and each of the first and second reference image sequences comprises a plurality of reference images determined at different time points;

acquiring, from the second reference image sequence corresponding to the first reference image sequence in the preset image library, a second reference image determined at the same time point as the first reference image; and determining a position of a tumor relative to the second ray source according to the second reference image.

In a second aspect, there is provided a tumor tracking device applied to radiation therapy equipment. The radiation therapy equipment includes a first ray source, a second ray source and a detector. When the first ray source is located at a first detection point, the second ray source is located at a second detection point. The device includes:

a first acquisition module, configured to acquire a detection image when the first ray source is located at the first detection point, wherein the detection image is an image determined when a radioactive ray, emitted by the first ray source at the first detection point toward a tumor area, is received by the detector;

a first determination module, configured to determine, from a first reference image sequence in a preset image library, a first reference image corresponding to the detection image, wherein the preset image library comprises the first reference image sequence and a second reference image sequence, the first reference image sequence is a reference image sequence determined based on an optical signal sent from a position of a first collection point toward the tumor area, the second reference image sequence is a reference image sequence determined based on an optical signal sent from a position of a second collection point toward the tumor area, the first detection point and the first collection point are at the same position relative to the tumor area, the second detection point and the second collection point are at the same position relative to the tumor area, and each of the first and second reference image sequences comprises a plurality of reference images determined at different time points;

a second acquisition module, configured to acquire, from the second reference image sequence corresponding to the first reference image sequence in the preset image library, a second reference image determined at the same time point as the first reference image; and a second determination module, configured to determine a position of a tumor relative to the second ray source according to the second reference image.

In a third aspect, there is provided a readable storage medium. Instructions are stored in the readable storage medium. When the readable storage medium runs on a processing component, the processing component is caused to execute the tumor tracking method of the present disclosure.

The beneficial effects of the technical solutions provided by the embodiments of the present disclosure are as follows. In the tumor tracking method and device, and the storage medium provided by the embodiments of the present disclosure, after a detection image when the first ray source is located at the first detection point is acquired, by determining, from the first reference image sequence in the preset image library, a first reference image corresponding to the detection image and acquiring, from a second reference image sequence corresponding to the first reference image sequence in the preset image library, a second reference image determined at the same time point as the first reference image, the position of the tumor relative to the second ray source can be determined according to the second reference image. As such, the tumor tracking can be achieved by only using radiation therapy equipment and less hardware equipment is required. Thus, by providing the novel tumor tracking device, the problem of high cost in tumor tracking can be solved, which facilitates the reduction of the tumor tracking cost.

BRIEF DESCRIPTION OF THE DRAWINGS

In order to describe the technical solutions in the embodiments of the present disclosure more clearly, the following briefly introduces the accompanying drawings required for describing the embodiments. Apparently, the accompanying drawings in the following description show merely some embodiments of the present disclosure, and a person of ordinary skill in the art may also derive other drawings from these accompanying drawings without creative efforts.

FIG. 3-1 is a flowchart of another tumor tracking method provided by an embodiment of the present disclosure;

FIG. 3-2 is a flowchart of a method for generating a preset image library provided by an embodiment of the present disclosure;

FIG. 3-3 is a schematic diagram of generating a preset image library provided by an embodiment of the present disclosure;

FIG. 3-4 is a flowchart of another method for generating the preset image library provided by an embodiment of the present disclosure;

FIG. 3-5 is a flowchart of yet another method for generating the preset image library provided by an embodiment of the present disclosure;

FIG. 3-6 is a schematic diagram of acquiring a reference image provided by an embodiment of the present disclosure;

FIG. 4 is a flowchart of another tumor tracking method provided by an embodiment of the present disclosure;

FIG. 5 is a flowchart of yet another tumor tracking method provided by an embodiment of the present disclosure;

FIG. 6-1 is a flowchart of yet another tumor tracking method provided by an embodiment of the present disclosure;

FIG. 6-2 is a flowchart of a method for predicting a tumor movement trajectory provided by an embodiment of the present disclosure;

FIG. 7-1 is a flowchart of another tumor tracking method provided by an embodiment of the present disclosure;

FIG. 7-2 is a flowchart of a method for determining an actual image sequence provided by an embodiment of the present disclosure;

FIG. 9-1 is a block diagram of a tumor tracking device provided by an embodiment of the present disclosure;

FIG. 9-2 is a block diagram of another tumor tracking device provided by an embodiment of the present disclosure.

DETAILED DESCRIPTION

In order to describe the objects, technical solutions and advantages of the present disclosure more clearly, the present disclosure will be described in detail below in combination with the accompanying drawings. Apparently, the described embodiments are merely some embodiments, rather than all embodiments, of the present disclosure. Based on the embodiments of the present disclosure, all other embodiments derived by a person of ordinary skill in the art without creative efforts shall fall within the protection scope of the present disclosure.

Figure 1:
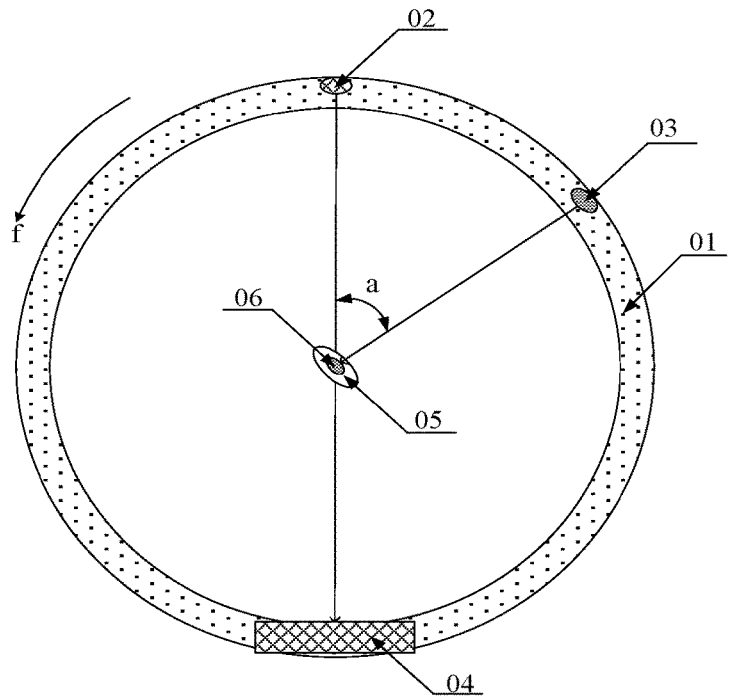
FIG. 1 is an application scenario diagram of radiation therapy equipment provided by an embodiment of the present disclosure.

FIG. 1 is an application scenario diagram of radiation therapy equipment according to an embodiment of the present disclosure. Referring to FIG. 1, the radiation therapy equipment includes: an equipment body 01, a first ray source 02, a second ray source 03 and a detector 04. The equipment body 01 is of a cylindrical structure. The first ray source 02, the second ray source 03 and the detector 04 are respectively arranged on the same circumference of the equipment body 01. A central angle corresponding to the arc between the first ray source 02 and the second ray sources 03 is a. The equipment body 01 can rotate about its own axis in a rotation direction f so as to drive the first ray source 02 and the second ray source 03 to rotate. In actual practice, the first ray source 02 may be an imaging source, and specifically, may be a diagnostic source. The second ray source 03 may be a treatment source, and specifically, may be a treatment head. With respect to the specific structures of the equipment body 01, the first ray source 02, the second ray source 03 and the detector 04, it may refer to the related art. Details thereof are not described herein for conciseness. The equipment body may also be a cantilever or a mechanical arm, which may also drive the first ray source and the second ray source to rotate along the same circumference.

Here, the first ray source 02 and the second ray source 03 can emit a radioactive ray. The detector 04 may be a flat panel detector, and can receive the radioactive ray emitted by the first ray source 02. It should be noted that the radiation therapy equipment further includes a processing component (not shown in FIG. 1) electrically connected to the first ray source 02, the second ray source 03 and the detector 04, respectively. The processing component may locate in a computer (such as a personal computer), and specifically, may be a processor of the computer, or the like. The processing component may determine a detection image based on the radioactive ray received by the detector 04.

As shown in FIG. 1, a tumor 06 grows in a patient 05. When the tumor 06 is a lung tumor, it may move in a regular way as the patient 05 breathes. When using the radiation therapy equipment, the patient 05 can be arranged in the equipment body 01 through a therapy bed (not shown in FIG. 1), keeping a fixed posture on the therapy bed, and maintaining a smooth and stable breathing. Then, the processing component may control the first ray source 02 to emit the radioactive ray to a tumor area (including the area of the tumor 06 and normal organs and tissues around the tumor 06). The radioactive ray passes through the tumor area to reach the detector 04, and is received by the detector 04. The detector 04 converts the received radioactive ray into an optical signal, and then converts the optical signal into an analog signal. The detector 04 may include an analog to digital converter (ADC) which converts the analog signal into a digital signal to be sent to the processing component. The processing component generates a detection image according to the received digital signal. The detection image may be a computed tomography (CT) image. After the detection image is generated, the processing component can determine, from a first reference image sequence in a preset image library, a first reference image corresponding to the detection image according to the detection image, and can acquire, from a second reference image sequence corresponding to the first reference image sequence in the preset image library, a second reference image determined at the same time point as the first reference image, and can determine the position of the tumor 06 relative to the second ray source 03 according to the second reference image, so that the movement of the tumor can be tracked. Further, a parameter of the second ray source 03 can be adjusted according to the position of the tumor 06 relative to the second ray source 03, and then the second ray source 03 is controlled to emit radioactive ray to the tumor 06. In the embodiment of the present disclosure, the first ray source 02 may be an imaging source; the second ray source 03 may be a treatment source; and the processing component can adjust at least one of a position parameter, a dose parameter and a radiation field parameter of the second ray source 03 according to the position of the tumor 06 relative to the second ray source 03.

Figure 2:
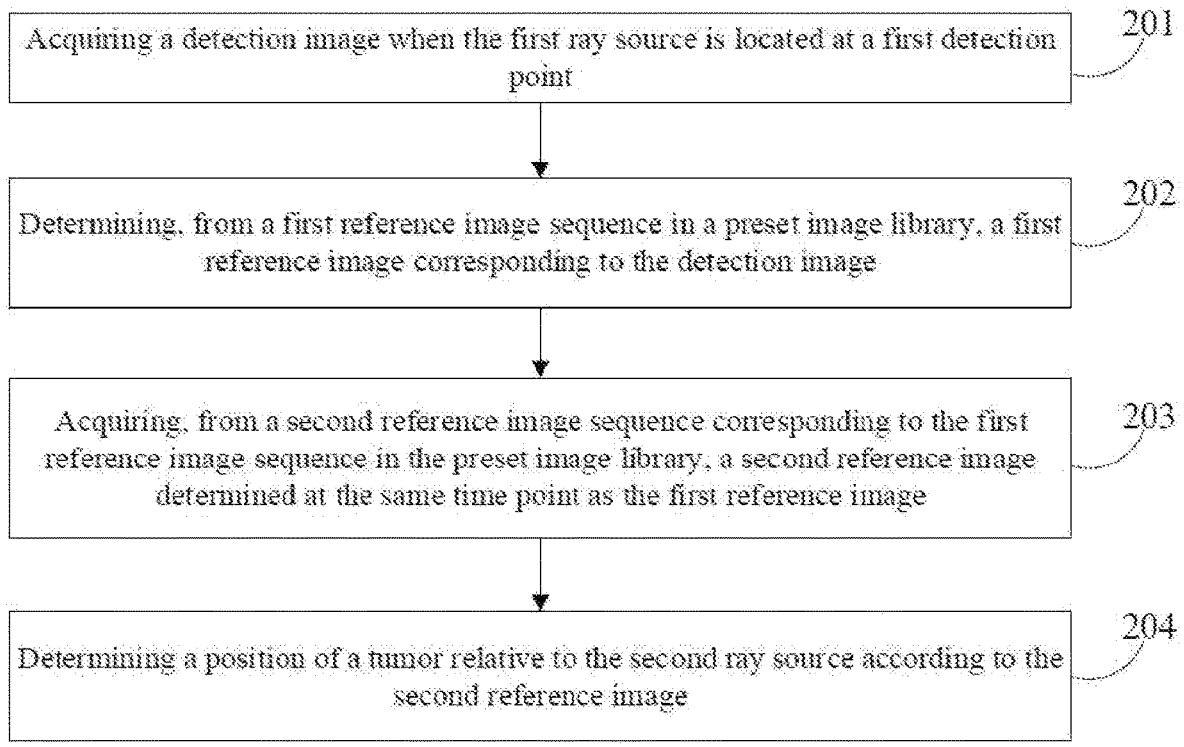
FIG. 2 is a flowchart of a tumor tracking method provided by an embodiment of the present disclosure.

FIG. 2 is a flowchart of a tumor tracking method according to an embodiment of the present disclosure. In the present embodiment, an example in which the tumor tracking method is applied to the radiation therapy equipment shown in FIG. 1 is taken for illustration. The radiation therapy equipment includes a first ray source, a second ray source and a detector. In the present disclosure, the tumor tracking method may be executed by a tumor tracking device which may be a functional unit in the processing component of the radiation therapy equipment. Referring to FIG. 2, the method includes the following steps.

In step 201, a detection image when the first ray source is located at a first detection point is acquired. The detection image is an image determined when a radioactive ray, emitted by the first ray source at the first detection point toward a tumor area, is received by the detector. Exemplarily, as shown in FIG. 1, the first ray source 02 is located at the first detection point, and the second ray source 03 is located at a second detection point. The first ray source 02 emits the radioactive ray when it is at the first position shown in the Figure, and the radioactive ray passes through the tumor in the human body and is received by the detector, so that a current tumor image, namely, the detection image, is determined.

In step 202, a first reference image corresponding to the detection image is determined from a first reference image sequence in a preset image library.

The preset image library includes the first reference image sequence and a second reference image sequence. The first reference image sequence is a reference image sequence determined based on an optical signal sent from a position of the first collection point toward the tumor area. The second reference image sequence is a reference image sequence determined based on an optical signal sent from a position of the second collection point toward the tumor area. The first detection point and the first collection point are at the same position relative to the tumor area. The second detection point and the second collection point are at the same position relative to the tumor area. Each of the first reference image sequence and the second reference image sequence includes a plurality of reference images determined at different time points.

It should be noted that the preset image library may be formed by collecting images. Taking FIG. 1 as an example, the first ray source 02 is located at the first detection point, and the second ray source 03 is located at the second detection point. In the embodiment of the present disclosure, when forming the preset image library, the first collection point may be located at the position of the first detection point of the first ray source 02 as shown in FIG. 1, and the second collection point may be located at the position of the second detection point of the second ray source 03 as shown in FIG. 1. Thus, the first collection point and the first detection point are at the same position relative to the tumor; and the second collection point and the second detection point are at the same position relative to the tumor.

Because the first reference image sequence in the preset image library includes a plurality of tumor images acquired at the first collection point at different time points, by determining the first reference image corresponding to the detection image from the first reference image sequence in the preset image library, position information of the tumor relative to the first detection point at this time can be determined.

Exemplarily, determining the first reference image corresponding to the detection image from the first reference image sequence in the preset image library can be implemented by comparing an image of the detection image with an image of each of the first reference images in the first reference image sequence in the preset image library to determine the first reference image corresponding to the detection image.

In step 203, a second reference image determined at the same time point as the first reference image is acquired from the second reference image sequence corresponding to the first reference image sequence in the preset image library.

The second reference image sequence includes a plurality of tumor images acquired at the second collection point at different time points. Each of the first reference image sequence and the second reference image sequence includes a plurality of reference images determined at different time points. Then, the second reference image determined according to the first reference image may be the second reference image of the tumor relative to the second detection point at this time.

It should be noted that the first reference image sequence includes a plurality of first reference images, and the second reference image sequence includes a plurality of second reference images. The first reference images and the second reference images may be provided with serial numbers, and a first reference image and a second reference image determined at the same time may have the same serial number, so as to facilitate the acquisition of the second reference image determined at the same time point as the first reference image. Of course, it may also be possible to directly use the determination time to show the corresponding first reference image sequence and second reference image sequence to facilitate the acquisition of the second reference image determined at the same time point as the first reference image. This is not limited in the present disclosure, and the above example is only illustrative.

In step 204, a position of a tumor relative to the second ray source is determined according to the second reference image.

In summary, in the tumor tracking method provided by the embodiment of the present disclosure, the first reference image sequence is formed with the plurality of the first reference images of the tumor which are collected at the first collection point at different time points, and the second reference image sequence is formed with the plurality of the second reference images of the tumor which are collected at the second collection point at different time points, so that the preset image library is formed. During the radiation therapy, the first ray source is located at the first detection point, and the second ray source is located at the second detection point. The first detection point and the first collection point correspond to each other in position relative to the tumor; and the second detection point and the second collection point correspond to each other in position relative to the tumor. After acquiring the detection image at the first detection point, the first reference image corresponding to the detection image is determined from the first reference image sequence in the preset image library; and correspondingly, the second reference image of the tumor relative to the second collection point at this time (equivalent to the second detection point at this time) is acquired according to the first reference image determined from the first reference image sequence. Thus, the position of the tumor relative to the second ray source can be determined according to the second reference image, thereby realizing the movement tracking of the tumor by the second ray source. Further, the second ray source can be adjusted according to the position of the tumor relative to the second ray source to enable the radioactive ray emitted by the second ray source to pass through the tumor area, so that damage to the normal tissues around the tumor can be avoided, while realizing tracked radiation on the tumor. In the tumor tracking method provided in the present disclosure, the tumor can be tracked by two ray sources and one detector of the radiation therapy equipment, so that there is no need to arrange two pieces of mutually-angled projection equipment. Thus, less hardware equipment is required, facilitating the reduction of the tumor tracking cost. In addition, compared with tracking tumor by marking the body surface of the patient, in the tumor tracking method provided in the present disclosure, the movement of tumor is directly tracked, so that the tracking accuracy is higher.

Figures 1, 3:
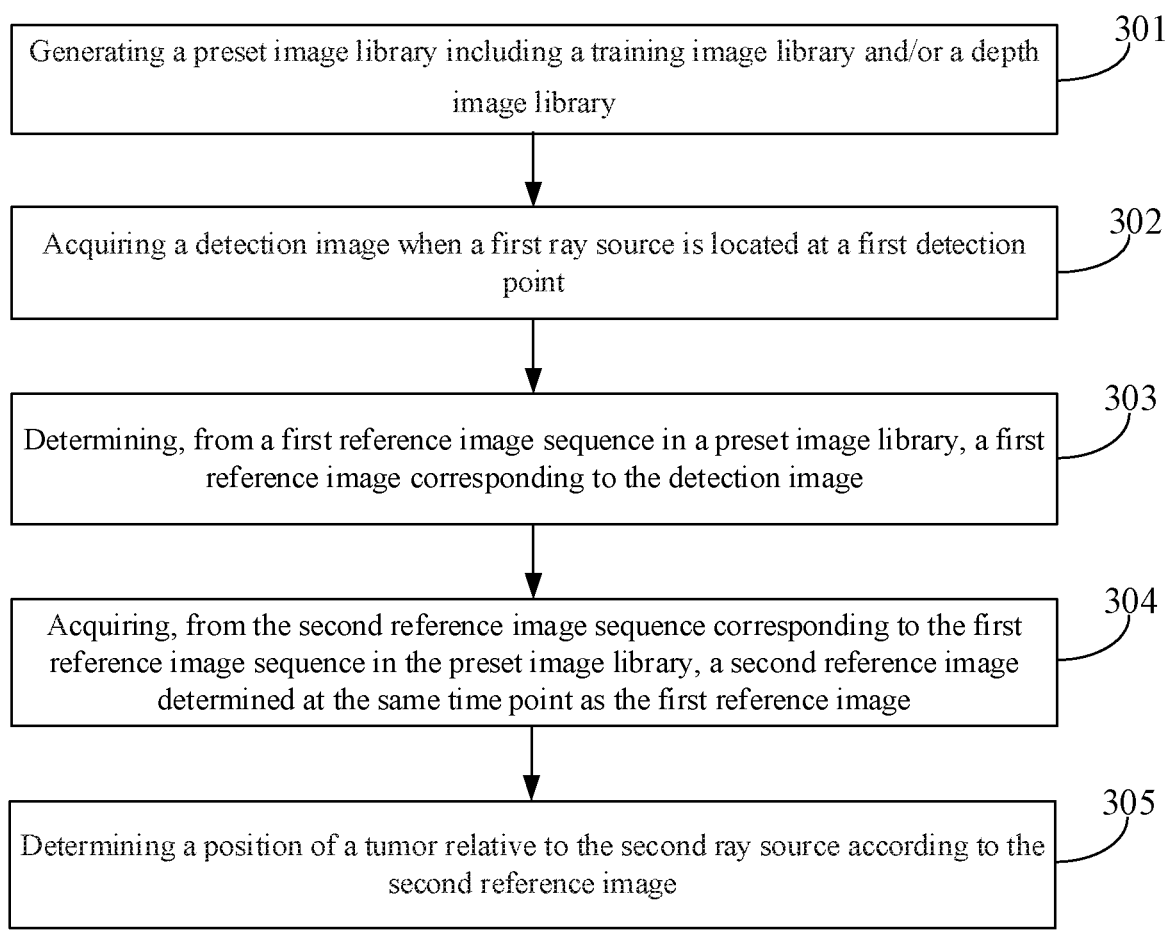
Figures 2, 3:
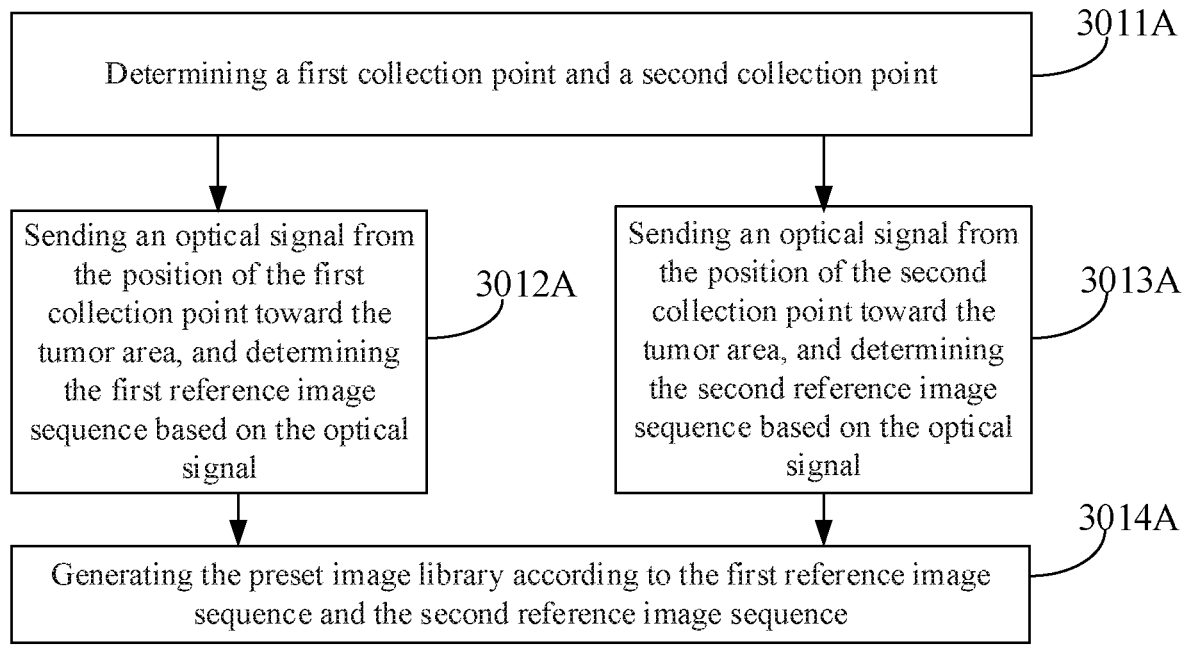
Figure 3:
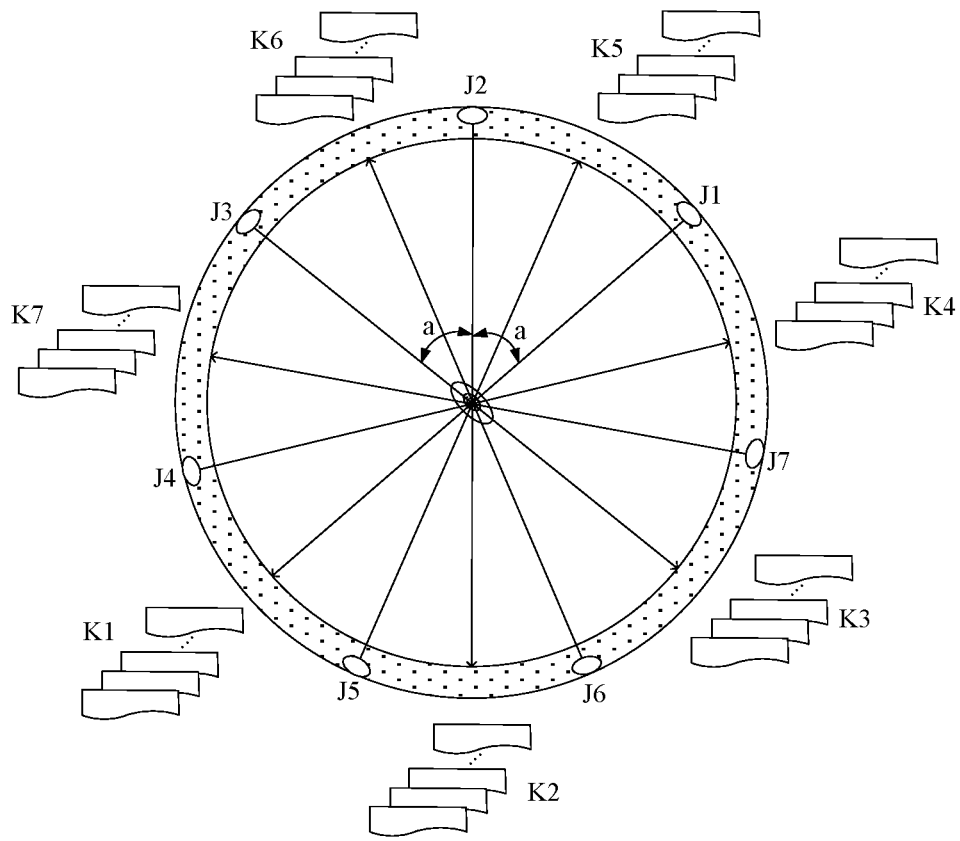

FIG. 3-1 is a flowchart of another tumor tracking method provided by an embodiment of the present disclosure. In the present embodiment, an example in which the tumor tracking method is applied to the radiation therapy equipment shown in FIG. 1 is taken for illustration. Referring to FIG. 3-1, the method includes the following steps.

In step 301, a preset image library including a training image library and/or a depth image library is generated.

In step 302, a detection image when a first ray source is located at a first detection point is acquired. The detection image is an image determined when a radioactive ray, emitted by the first ray source at the first detection point toward a tumor area, is received by the detector.

In step 303, a first reference image corresponding to the detection image is determined from a first reference image sequence in the preset image library.

In step 304, a second reference image determined at the same time point as the first reference image is acquired from the second reference image sequence corresponding to the first reference image sequence in the preset image library.

In step 305, a position of a tumor relative to the second ray source is determined according to the second reference image. That is, the movement of the tumor is tracked by the second ray source.

Compared with the embodiment shown in FIG. 2, in the embodiment shown in FIG. 3-1, prior to determining, from the first reference image sequence in the preset image library, the first reference image corresponding to the detection image, the method further includes: generating the preset image library.

The above step 301 is specifically described. In step 301, the preset image library includes the training image library and/or the depth image library. That is, the preset image library may include the training image library, or may include the depth image library, or may include the training image library and the depth image library. The preset image library may include a plurality of reference image sequence groups, and each of the reference image sequence groups includes one first reference image sequence and one second reference image sequence. Taking an example in which the first ray source and the second ray source of the radiation therapy equipment are capable of rotating circumferentially around the tumor area, on one rotation circumference, the first ray source and the second ray source may be located at a plurality of preset detection stations; and each of the preset detection stations includes one first detection point and one second detection point, and each of the preset detection stations corresponds to one of the reference image sequence groups. That is, the first detection point of each preset detection station and the first collection point corresponding to one reference image sequence group have a corresponding position relative to the tumor, and thus, the preset detection station corresponds to the first reference image sequence. Similarly, the second detection point of each preset detection station and the second collection point corresponding to one reference image sequence group have a corresponding position relative to the tumor, and thus, the preset detection station corresponds to the second reference image sequence. Therefore, during the process that the first ray source and the second ray source move along the circumference, the position of the tumor can be continuously tracked.

It should be noted that, in the present embodiment, the position of each preset detection station is not specifically limited. For example, the preset detection stations may be arranged every 2 s (or 4 s, 5 s, etc.), or may be arranged with a rotational central angle of every 5° (or 8°, 10°, 15°, etc.).

In the embodiment of the present disclosure, the reference image sequence in the training image library may be an image sequence determined when the patient is under breathing training (training the patient to obtain his/her smooth and steady breathing). Each reference image sequence in the training image library includes n reference images determined at n different time points; and n>1, and n is an integer. The reference image sequence in the depth image library may be an image sequence determined when the patient is taking a deep breath. Each reference image sequence in the depth image library includes p reference images determined at p different time points; and p>n, and p is an integer. The specific values of n and p can be determined according to a deep breathing cycle and a trained breathing cycle, and are not limited in the embodiment of the present disclosure.

The preset image library can be obtained by using existing CT equipment or other imaging equipment. The present disclosure does not limit the specific methods and steps for obtaining the preset image library, and several examples are listed below for illustration.

Exemplarily, FIG. 3-2 is a flowchart of a method for generating a preset image library according to an embodiment of the present disclosure. Referring to FIG. 3-2, the method includes the following sub-steps.

In sub-step 3011A, a first collection point and a second collection point are determined.

It should be noted that, in the present disclosure, the first collection point and the first detection point are at the same position relative to the tumor area, and the second collection point and the second detection point are at the same position relative to the tumor area. Thus, the positions of the first collection point and the second collection point relative to the tumor area may be first determined, and then, the positions of the first detection point and the second detection point are determined. It is also possible that the positions of the first detection point and the second detection point relative to the tumor area are first determined, and then, the positions of the first collection point and the second collection point are determined.

In the present disclosure, there may be a plurality of first collection points and a plurality of second collection points. Exemplarily, in the embodiment of the present disclosure, a plurality of collection point groups may be determined. Each collection point group includes one first collection point and one second collection point. Correspondingly, the preset image library may include a plurality of reference image sequence groups. Each reference image sequence group corresponds to one collection point group, and thus includes one first reference image sequence and one second reference image sequence. The first collection point in each collection point group and the first detection point are at the same position relative to the tumor area; and the second collection point in each collection point group and the second detection point are at the same position relative to the tumor area. Therefore, the central angle corresponding to the arc between the first collection potion and the second collection point in each collection potion group is equal to the central angle corresponding to the arc between the first detection point and the second detection point.

Exemplarily, determining the first collection point and the second collection point may be implemented by sequentially placing a patient in the equipment body of the radiation therapy equipment through the therapy bed to enable the patient to keep a fixed posture on the therapy bed and maintain the smooth, stable and deep breathing, determining a breathing cycle (deep breathing cycle or trained breathing cycle) of the patient, a characteristics of a tumor in the patient, movement of the tumor in the patient, and the like, and setting the collection point group according to the breathing cycle of the patient, the characteristics of the tumor in the patient, the movement of the tumor in the patient and the like. For example, when the tumor moves in a first direction (such as an x-axis direction), one collection point (the first collection point or the second collection point) may be disposed in a second direction (such as a y-axis direction) perpendicular to the first direction. According to a relationship between the first collection point and the second collection point, another collection point is disposed, so that the collection point group can be disposed to subsequently collect an image during the movement of the tumor. Exemplarily, the relationship between the first collection point and the second collection point may be that the central angle corresponding to the arc between the first collection point and the second collection point is 5°, 10°, 15°, or 20°. The specific relationship such as the degree of the central angle is not limited in the present disclosure, and the above description is only used as an example for illustration.

In the present disclosure, exemplarily, the central angle corresponding to the arc between the first collection potion and the second collection point is equal to the central angle corresponding to the arc between the first ray source and the second ray source of the radiation therapy equipment. For example, when the central angle corresponding to the arc between the first ray source and the second ray source of the radiation therapy equipment is a, the central angle corresponding to the arc between the first collection point and the second collection point in each collection point group is equal to a.

Further, the central angle corresponding to the arc between the first collection point and the second collection point in each collection point group is equal to a central angle corresponding to an arc between two first collection points in any two adjacent collection point groups. Or, the central angle corresponding to the arc between the first collection point and the second collection point in each collection point group is equal to a central angle corresponding to an arc between two second collection points in any two adjacent collection point groups. Thus, one of the collection points can be shared in two different collection point groups, so that the number of collection points as disposed can be reduced. Correspondingly, the central angle corresponding to the arc between the first detection point and the second detection point in each preset detection station is equal to a central angle corresponding to an arc between the first detection points in any two adjacent preset detection stations. Or, the central angle corresponding to the arc between the first detection point and the second detection point in each preset detection station is equal to a central angle corresponding to an arc between the second detection points in any two adjacent preset detection stations.

Exemplarily, FIG. 3-3 is a schematic diagram of generating a preset image library provided by an embodiment of the present disclosure. Referring to FIG. 3-3, the plurality of collection points includes seven collection points J1 to J7 which are located on the same circumference of the equipment body of the radiation therapy equipment (not shown in FIG. 3-3). The seven collection points can form seven collection point groups. Exemplarily, the collection points J1 and J2 can form a first collection point group; and the collection points J2 and J3 can form a second collection point group. In the first collection point group, the collection point J1 is the second collection point; the collection point J2 is the first collection point; and a central angle corresponding to an arc between the collection point J1 and the collection point J2 is equal to a. In the second collection point group, the collection point J2 is the second collection point; the collection point J3 is the first collection point; and a central angle corresponding to an arc between the collection point J2 and the collection point J3 is equal to a. A central angle corresponding to an arc between the two first collection points (namely, the collection points J2 and J3) in the first and second collection point groups is equal to a. A central angle corresponding to an arc between the two second collection points (namely, the collection points J1 and J2) in the first and second collection point groups is equal to a. As the collection point J2 is shared as the first collection point and the second collection point, the number of the collection points as disposed is reduced. Of course, the collection points J3 and J4 can form one collection point group, the collection points J3 and J5 can form one collection point group, and so on.

In sub-step 3012A, an optical signal is sent from the position of the first collection point toward the tumor area, and the first reference image sequence is determined based on the optical signal.

After the first collection point and the second collection point are determined, a bulb tube of imaging equipment (generally including the bulb tube and a flat panel detector) can continuously send optical signals toward the tumor area from the position of the first collection point. The flat panel detector determines each reference image based on the received optical signals to obtain the first reference image sequence. Exemplarily, the imaging equipment may also be the CT equipment.

Exemplarily, when generating the training image library, in step 3012A, the patient maintains the smooth and stable breathing. The tumor tracking device can control the imaging equipment to continuously send, from the position of the first collection point toward the tumor area, optical signals for n times, and determines a reference image based on each of the n received optical signals to obtain the first reference image sequence. The first reference image sequence includes n reference images. When generating the depth image library, the patient maintains the deep breathing.

In sub-step 3013A, an optical signal is sent from the position of the second collection point toward the tumor area, and the second reference image sequence is determined based on the optical signal.

Exemplarily, after the first and second collection points are determined, a piece of imaging equipment may be deployed at the position of each of the collection points (including the first and second collection points). That is, one bulb tube is arranged at each of the first collection point and the second collection point, and corresponds to one flat panel detector. Thus, optical signals can be continuously sent toward the tumor area from the position of the second collection point while the first reference image sequence is collected at the first collection point. In addition, a reference image is determined based on each of the plurality of received optical signals to obtain the second reference image sequence.

Of course, there may be one piece of the imaging equipment. That is, one ray source (the bulb tube) and one flat panel detector are included. When the bulb tube is located at the first collection point, the flat panel detector receives a ray beam emitted by the bulb tube at the first collection point to acquire the first reference image sequence. Then, the bulb tube is moved to the second collection point, and the flat panel detector receives a ray beam emitted by the bulb tube at the second collection point to acquire the second reference image sequence.

Similarly, when generating the training image library, the patient maintains the smooth and stable breathing to obtain the second reference image sequence. When generating the depth image library, the patient maintains the deep breathing to obtain the second reference image sequence.

In sub-step 3014A, the preset image library is generated according to the first reference image sequence and the second reference image sequence.

After determining the first and second reference image sequences, the tumor tracking device can generate a preset image library according to the first and second reference image sequences.

It should be noted that, in a practical application, after generating the preset image library, the tumor tracking device can further store an index relationship between the collection points and the reference image sequences, so as to subsequently determine a reference image sequence and a reference image according to the index relationship. The index relationship records a one-to-one correspondence between information (for example, identifiers) of the collection points and information (for example, identifiers) of the reference image sequences, and is configured to indicate the one-to-one correspondence between the collection points and the reference image sequences. In the index relationship, the information of the reference images with the same determination time may be stored correspondingly; and further, the determination times of the reference images may also be stored in the index relationship. In the embodiment of the present disclosure, the preset image library includes the training image library and/or the depth image library. The index relationship of the training image library generated by the tumor tracking device based on the seven collection points J1 to J7 can be shown as Table 1 below. The index relationship of the depth image library can be shown as Table 2 below.

TABLE 1

(Training image Library)

| Collection Point | J1 | J2 | J3 | J4 | ... | J7 |
|---|---|---|---|---|---|---|
| Reference Image Sequence | K1 | K2 | K3 | K4 | ... | K7 |
| t1 | K11 | K21 | K31 | K41 | ... | K71 |
| t2 | K12 | K22 | K32 | K42 | ... | K77 |
| t3 | K13 | K23 | K33 | K43 | ... | K73 |
| t4 | K14 | K24 | K34 | K44 | ... | K74 |
| ... | ... | ... | ... | ... | ... | ... |
| tn | K1n | K2n | K3n | K4n | ... | K7n |

TABLE 2

(Depth Image Library)

| Collection Point | J1 | J2 | J3 | J4 | ... | J7 |
|---|---|---|---|---|---|---|
| Reference Image Sequence | K1 | K2 | K3 | K4 |  | K7 |
| t1 | K11 | K21 | K31 | K41 | ... | K71 |
| t2 | K12 | K22 | K32 | K42 | ... | K72 |
| t3 | K13 | K23 | K33 | K43 | ... | K73 |
| t4 | K14 | K24 | K34 | K44 | ... | K74 |
| ... | ... | ... | ... | ... | ... | ... |
| tn | K1n | K2n | K3n | K4n | ... | K7n |
| t(n + 1) | K1(n + 1) | K2(n + 1) | K3(n + 1) | K4(n + 1) | ... | K7(n + 1) |
| ... | ... | ... | ... | ... | ... | ... |
| tp | K1p | K2p | K3p | K4p | ... | K7p |

It can be seen from Table 1 that in the training image library, each reference image sequence includes n reference images determined at n different time points. For example, the reference image sequence K1 includes n reference images K11 to K1n determined at n different time points from t1 to tn, the reference image sequence K2 includes n reference images K21 to K2n determined at n different time points from t1 to tn and so on. It can be seen from Table 2 that in the depth image library, each reference image sequence includes p reference images determined at p different time points. For example, the reference image sequence K1 includes p reference images K11 to K1p determined at p different time points from t1 to tp, the reference image sequence K2 includes p reference images K21 to K2p determined at p different time points from t1 to tp, and so on.

In the above Table 1 and Table 2, the reference image sequence K1 and the reference image sequence K2 may form a reference image sequence group, in which the reference image sequence K2 may be the first reference image sequence and the reference image sequence K1 may be the second reference image sequence. The reference image sequence K2 and the reference image sequence K3 may form a reference image sequence group, in which the reference image sequence K3 may be the first reference image sequence and the reference image sequence K2 may be the second reference image sequence. The reference image sequence K3 and the reference image sequence K4 may form a reference image sequence group, in which the reference image sequence K4 may be the first reference image sequence and the reference image sequence K3 may be the second reference image sequence, and so on. It should be noted that in the embodiment of the present disclosure, Kab represents a reference image, wherein a represents that the reference image sequence of the reference image Kab is Ka; and b represents the serial number of the reference image Kab in the reference image sequence Ka. In Table 1, $1 \leq a \leq 7$, and $1 \leq b \leq n$. In Table 2, $1 \leq a \leq 7$, and $1 \leq b \leq p$. In addition, both a and b are integers.

Figures 3, 4:
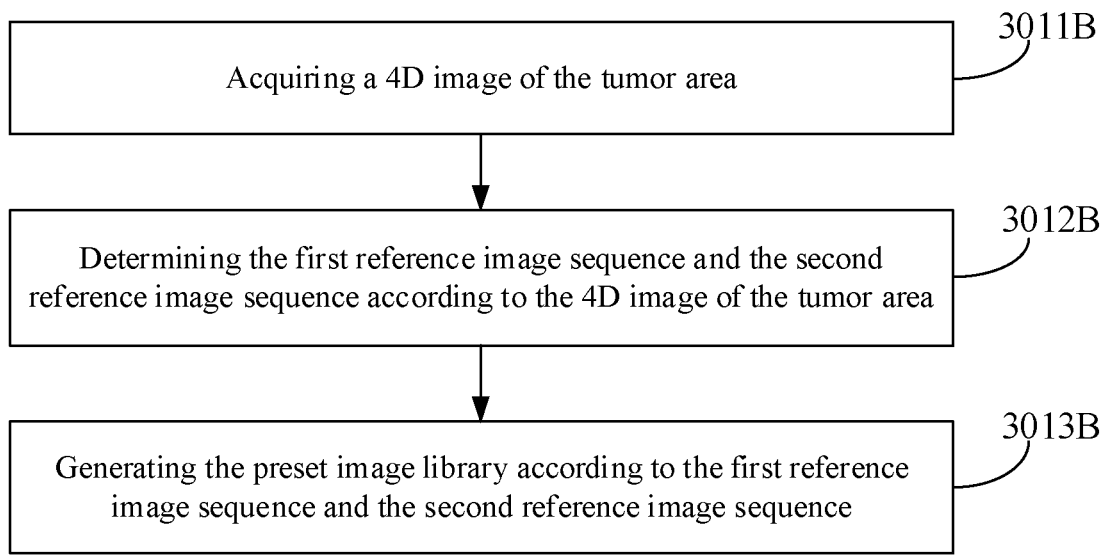

Exemplarily, FIG. 3-4 is a flowchart of another method for generating a preset image library according to an embodiment of the present disclosure. Referring to FIG. 3-4, the method includes the following sub-steps.

In sub-step 3011B, a 4D image of the tumor area is acquired.

The tumor tracking device can acquire the 4D image of the tumor area through four-dimension computed tomography (4DCT) equipment. Optionally, the tumor tracking device controls the 4DCT equipment to expose the tumor area to acquire the 4D image of the tumor area. The specific implementation process of exposing of the tumor area by the 4DCT equipment can refer to the related art, and is not repeated in the embodiment of the present disclosure.

In sub-step 3012B, the first reference image sequence and the second reference image sequence are determined according to the 4D image of the tumor area.

In the embodiment of the present disclosure, the 4D image of the tumor area is an image sequence including spatial position coordinates of the tumor area and time information. Exemplarily, the determining the first collection point and the second collection point, that is, the determining the position of the collection points relative to the tumor, may include extracting the reference image sequences from the 4D image to obtain the first reference image sequence corresponding to the first collection point and the second reference image sequence corresponding to the second collection point.

It should be noted that the tumor tracking device may extract a plurality of reference image sequence groups from the 4D image. Each reference image sequence group may include one first reference image sequence and one second reference image sequence. A process of determining, by the tumor tracking device, the first reference image sequence and the second reference image sequence from the 4D image may refer to the related art, and is not repeated in the embodiment of the present disclosure.

In sub-step 3013B, the preset image library is generated according to the first reference image sequence and the second reference image sequence. A specific implementation process of step 3013B may refer to the foregoing sub-step 3014A, and is not repeated by the embodiment of the present disclosure.

Figures 3, 4, 5:
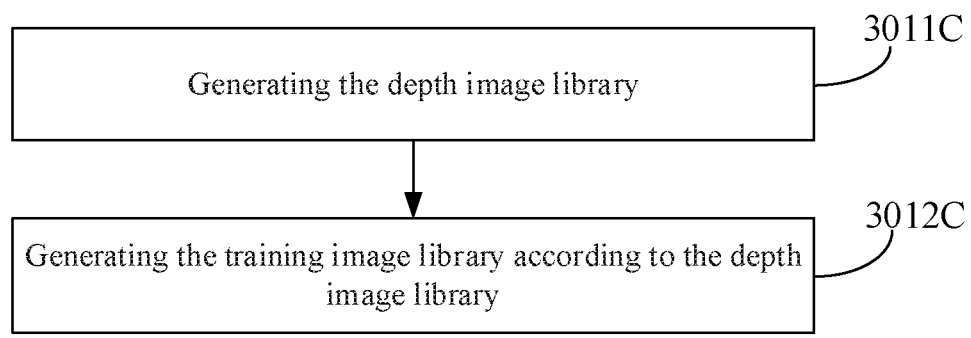

It should be noted that in a practical application, as the breathing depth of the deep breathing is greater than the breathing depth of the trained breathing (smooth and stable breath), the breathing duration of the deep breathing is longer than the breathing duration of the trained breathing. Thus, the number of images in the reference image sequence of the depth image library is greater than that of images in the reference image sequence of the training image library. That is, if the reference image sequence is regarded as a reference image set, each reference image set in the training image library may be a subset of the reference image set in the depth image library. Therefore, in the embodiment of the present disclosure, based on the known depth image library, the tumor tracking device can further generate the training image library according to the depth image library. Specifically, FIG. 3-5 is a flowchart of a yet another method for generating a preset image library according to an embodiment of the present disclosure. Referring to FIG. 3-5, the method includes the following sub-steps.

In sub-step 3011C, the depth image library is generated.

Exemplarily, the method shown in FIG. 3-2 or FIG. 3-4 may be adopted to generate the depth image library. The specific implementation process may refer to the related description in FIG. 3-2 or FIG. 3-4, and is not repeated in the embodiment of the present disclosure.

In sub-step 3012C, the training image library is generated according to the depth image library.

Exemplarily, a reference collection point may be determined from the first and second collection points. Then, an optical signal is sent toward the tumor area from the position of the reference collection point, and a reference image sequence is determined based on the optical signal. A sub-reference image sequence is acquired from the reference image sequence in the depth image library according to the reference image sequence. According to the acquired sub-reference image sequence, other sub-reference image sequences are acquired from other reference image sequences in the depth image library. The sub-reference image sequence acquired from the first reference image sequence in the depth image library is used as the first sub-reference image sequence. The sub-reference image sequence acquired from the second reference image sequence in the depth image library is used as the second sub-reference image sequence. In addition, the first and second sub-reference image sequences acquired from the first and second reference image sequences in one reference image sequence group in the depth image library are used as one sub-reference image sequence group. In this way, a plurality of sub-reference image sequence groups are obtained; and further, the training image library is generated according to the plurality of sub-reference image sequence groups.

It should be noted that after generating the depth image library and the training image library, the tumor tracking device can further store information related to the depth image library and the training image library. The specific implementation process may refer to the above Table 1 and Table 2 and related description, and is not repeated in the embodiment of the present disclosure. Of course, the training image library may also be generated according to multiple different manners based on the depth image library, which is not limited in the present disclosure, and which is illustrated only by taking the above as an example.

Step 302 will be specifically described in combination with step 301. A detection image when the first ray source is located at the first detection point is acquired, and is an image determined when the radioactive ray, emitted by the first ray source at the first detection point toward the tumor area, is received by the detector.

In the embodiment of the present disclosure, the first detection point and the first collection point are at the same position relative to the tumor area.

As shown in FIG. 3-6 and FIG. 3-3, the first detection point in FIG. 3-6 may be the collection point J2 (namely, the first collection point) shown in FIG. 3-3. A patient can be arranged in an equipment body 01 of radiation therapy equipment through the therapy bed (not shown in FIG. 3-6), keeping a fixed posture on the therapy bed, and maintaining the smooth and stable breathing. Then, the equipment body 01 is controlled to rotate about its own axis in the rotation direction f. When rotating to the first detection point (the collection point J2), the first ray source 02 is controlled to emit the radioactive ray toward the tumor area (not shown in FIG. 3-6). The radioactive ray passes through the tumor area to reach the detector 04. After receiving the radioactive ray, the detector 04 converts the radioactive ray into an optical signal, and then converts the optical signal into a digital signal. The tumor tracking device generates the detection image according to the digital signal. In the embodiment of the present disclosure, the first detection point and the first collection point are at the same position relative to the tumor area, and the second detection point and the second collection point are at the same position relative to the tumor area. Thus, when the first ray source 02 is rotated to the first detection point, the second ray source 03 is located at the second detection point. The second detection point may be the collection point J1 shown in FIG. 3-6.

Taking the tumor tracking method shown in FIG. 3-1 as an example to make a specific illustration. That is, as shown in FIG. 4 which shows another tumor tracking method provided by the present disclosure, the method includes the following steps.

In step 401, a preset image library including a training image library and/or a depth image library is generated. The specific process may refer to step 301 shown in FIG. 3-1, and is not repeated herein.

In step 402, a detection image when a first ray source is located at a first detection point is acquired. The detection image is an image determined when a radioactive ray, emitted by a first ray source at a first detection point toward a tumor area, is received by a detector. The specific process may refer to step 302 shown in FIG. 3-1, and is not repeated herein.

In step 403, whether a first reference image corresponding to the detection image exists in a first reference image sequence in the training image library is judged.

When the first reference image corresponding to the detection image exists in the first reference image sequence in the training image library, the following steps 404 and 405 are executed.

Exemplarily, the training image library is taken as an example. In the embodiment of the present disclosure, as shown in FIG. 3-6, the first detection point may be the collection point J2. The first reference image sequence corresponding to the collection point J2 (the first detection point) in the training image library is the reference image sequence K2 including n reference images K21 to K2n. The tumor tracking device may first determine the detection image, and then compares the detection image with each of the reference images K21 to K2n to judge whether a first reference image having the same picture as the detection image exists in the first reference image sequence K2 in the training image library.

In step 404, the first reference image corresponding to the detection image is determined from the first reference image sequence in the training image library. The specific process may refer to step 303 shown in FIG. 3-1, and is not repeated herein.

Exemplarily, the first reference image corresponding to the detection image in the first reference image sequence K2 in the training image library may be the reference image K21. Thus, the reference image K21 is determined from the first reference image sequence K2 in the training image library.

In step 405, a second reference image determined at the same time point as the first reference image is acquired from the second reference image sequence corresponding to the first reference image sequence in the training image library. The specific process may refer to step 304 shown in FIG. 3-1, and is not repeated herein.

Exemplarily, in the embodiment of the present disclosure, as shown in FIG. 3-6, the reference image sequence corresponding to the second detection point (the collection point J1) may be the reference image sequence K1. The reference image sequence K1 is used as the second reference image sequence corresponding to the first reference image sequence (the reference image sequence K2). Then, the second reference image determined at the same time point as the first reference image is acquired from the reference image sequence K1.

Exemplarily, in the embodiment of the present disclosure, the first reference image may be the reference image K21, and the reference image determined at the same time point as the reference image K21 in the second reference image sequence K1 may be the reference image K11. Thus, the reference image K11 is used as the second reference image corresponding to the first reference image K21.

When there is no first reference image corresponding to the detection image in the first reference image sequence in the training image library, the following steps 406 and 407 are executed.

In step 406, the first reference image is determined from the first reference image sequence in the depth image library. The specific process may refer to step 303 shown in FIG. 3-1, and is not repeated herein.

In step 407, a second reference image determined at the same time point as the first reference image is acquired from the second reference image sequence corresponding to the first reference image sequence in the depth image library. The specific process may refer to step 304 shown in FIG. 3-1, and is not repeated herein.

In step 408, a position of a tumor relative to the second ray source is determined according to the second reference image.

In the above embodiment provided by the present disclosure, when the preset image library includes the depth image library and the training image library, the reference image is preferentially determined from the training image library. This is because compared with the deep breathing, the tumor moves in a more stable way during the smooth and stable breathing, which would be more conducive to tracking.

Of course, in the embodiment shown in FIG. 2, after acquiring the detection image when the first ray source is located at the first detection point, prior to determining the position of the tumor relative to the second ray source according to the second reference image, the method further includes: judging whether a first reference image corresponding to the detection image exists in the first reference image sequence in the training image library. The present disclosure only takes FIG. 4 as an example for illustration.

It should be noted that in the embodiment shown in FIG. 4, the training image library may further include a plurality of reference image sequence groups. The specific process may refer to the description in the embodiment shown in FIG. 3-1, and is not repeated herein.

Another tumor tracking method provided by the present disclosure is described by taking the method shown in FIG. 2 as an example. FIG. 5 shows another implementation of the method provided by the present disclosure. Referring to FIG. 5, the method includes the following steps.

In step 501, a detection image when a first ray source is located at a first detection point is acquired. The detection image is an image determined when a radioactive ray, emitted by the first ray source at the first detection point toward a tumor area, is received by a detector.

In step 502, a first reference image corresponding to the detection image is determined from a first reference image sequence in a preset image library.

In step 503, a second reference image determined at the same time point as the first reference image is acquired from a second reference image sequence corresponding to the first reference image sequence in the preset image library.

In step 504, a position of a tumor relative to the second ray source is determined according to the second reference image.

In step 505, a parameter of the second ray source is adjusted according to the position of the tumor relative to the second ray source.

Steps 501 to 504 may refer to the specific description of the embodiment shown in FIG. 2, and is not repeated herein. In step 505, the parameter of the second ray source is further adjusted, so that the second ray source emits the radioactive ray toward the tumor according to the adjusted parameter to conduct tracked radiation on the tumor according to the position of the tumor, thereby avoiding radiating the normal tissue, and reducing damage to the normal tissues.

That is, in the above implementation provided by the present disclosure, after determining the position of the tumor relative to the second ray source according to the second reference image, the method further includes adjusting the parameter of the second ray source according to the position of the tumor relative to the second ray source, thereby enabling the second ray source to precisely track the position of the tumor in movement.

In the embodiment of the present disclosure, the first ray source may be an imaging source, and the second ray source may be a treatment source. Adjusting, by the tumor tracking device, the parameter of the second ray source according to the position of the tumor relative to the second ray source may include: adjusting, by the tumor tracking device, at least one of a position parameter, a dose parameter and a radiation field parameter of the second ray source according to the position of the tumor relative to the second ray source. Optionally, the treatment source may be a treatment head. The treatment head may include a ray source and a multi-leaf collimator. The ray source is configured to emit a radioactive ray. The multi-leaf collimator is configured to generate a radiation field that meets a requirement. The radiation field refers to the range of the radioactive ray radiated to the body surface of the patient. By controlling the multi-leaf collimator to generate parameters such as the radiation field and the dose that meet the requirement, after controlling the second ray source to emit the radioactive ray toward the tumor, the radioactive ray emitted from the second ray source can be radiated, through the radiation field generated by the multi-leaf collimator, toward the tumor to track the tumor, thereby realizing more precise radiation therapy. The implementation process of adjusting the parameter of the second ray source according to the position of the tumor relative to the second ray source may lie in adjusting the radiation field formed by the multi-leaf collimator. The specific manners may refer to the related art, and is not repeated in the embodiment of the present disclosure.

It should be noted that in a practical application, for any one of the first detection points, the above step may be repeatedly executed, so as to track and treat the tumor in real time in the whole radiation therapy process. In addition, the method shown in FIG. 5 only takes the embodiment shown in FIG. 2 as an example. It can be understood that it can also be applied in any one of the tracking methods provided in the present disclosure. For example, it can be applied in the method shown in FIG. 3-1 or FIG. 4. In the present disclosure, the method shown in FIG. 5 is only shown as an example. Other implementations may be derived from the method shown in FIG. 5, and are not repeated herein.

Figures 3, 4, 5, 6:
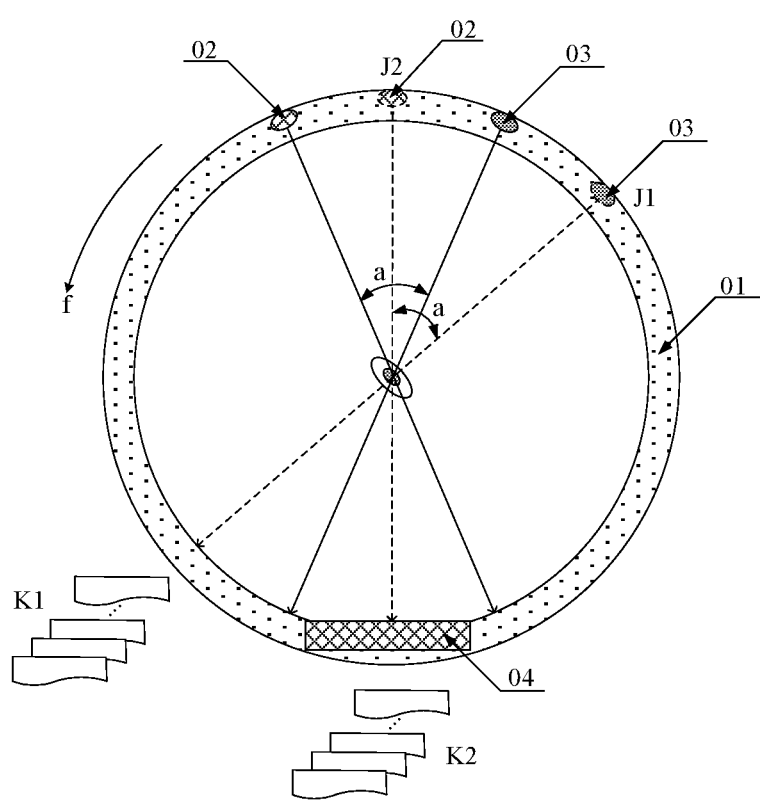
Figure 4:
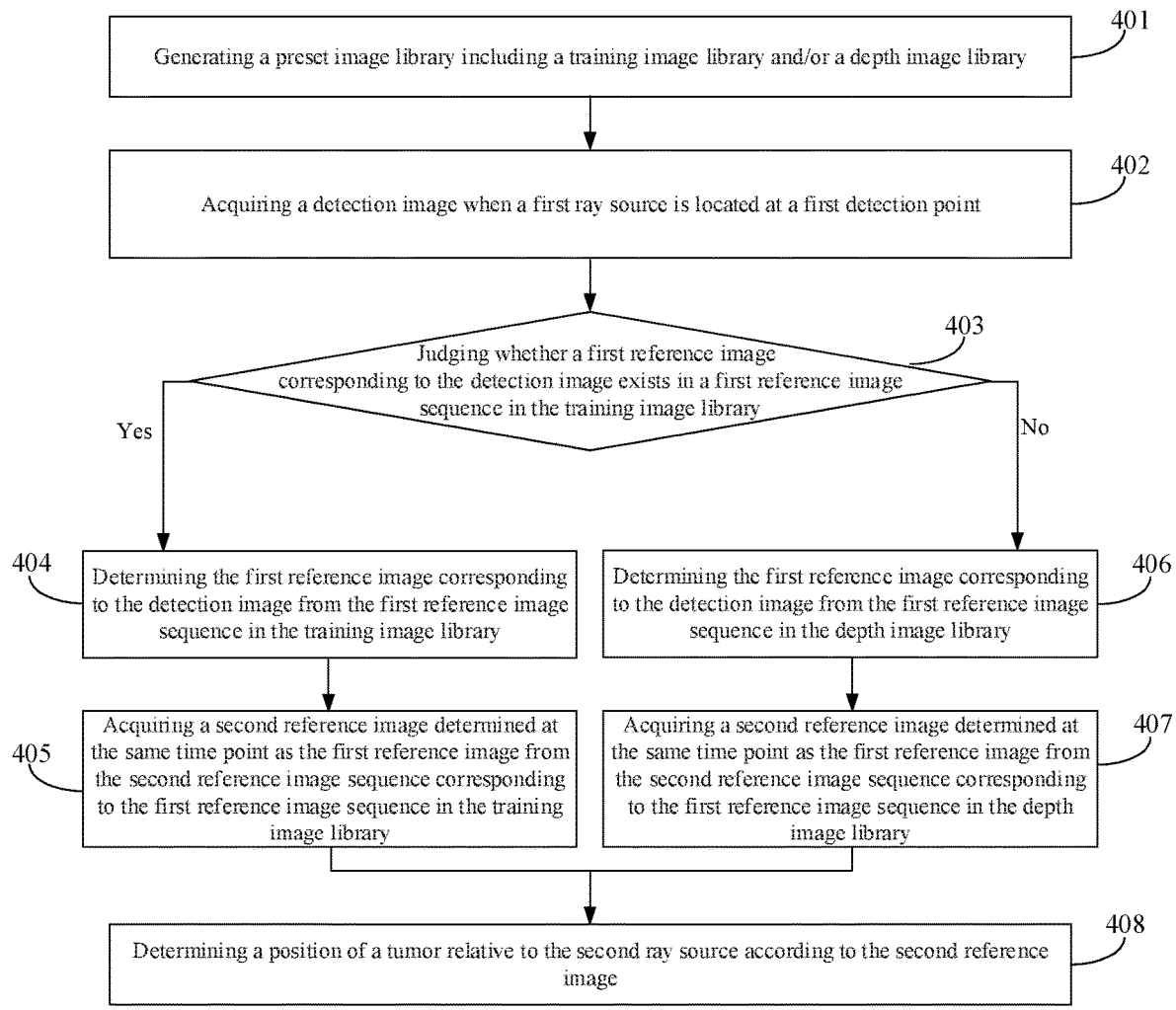
Figure 5:
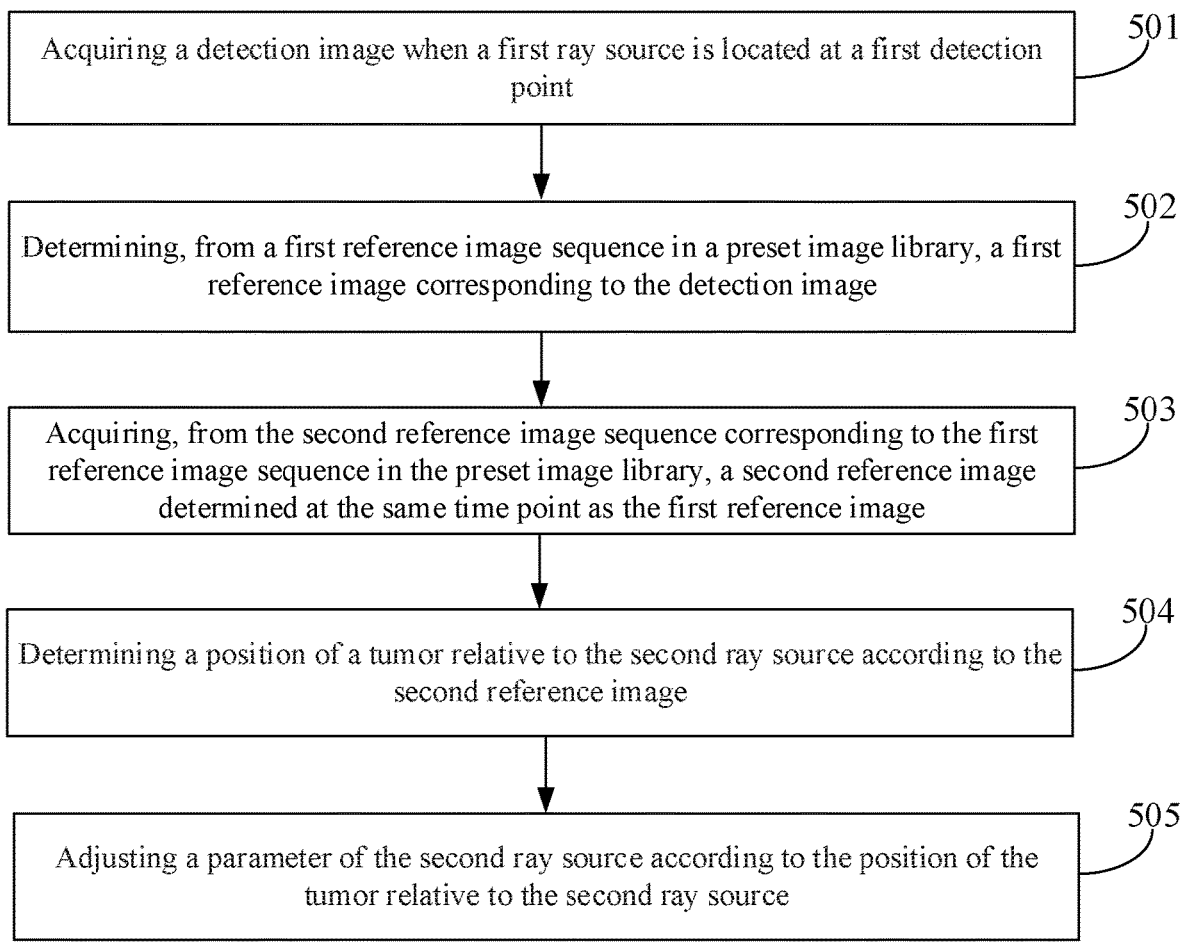
Figures 1, 6:
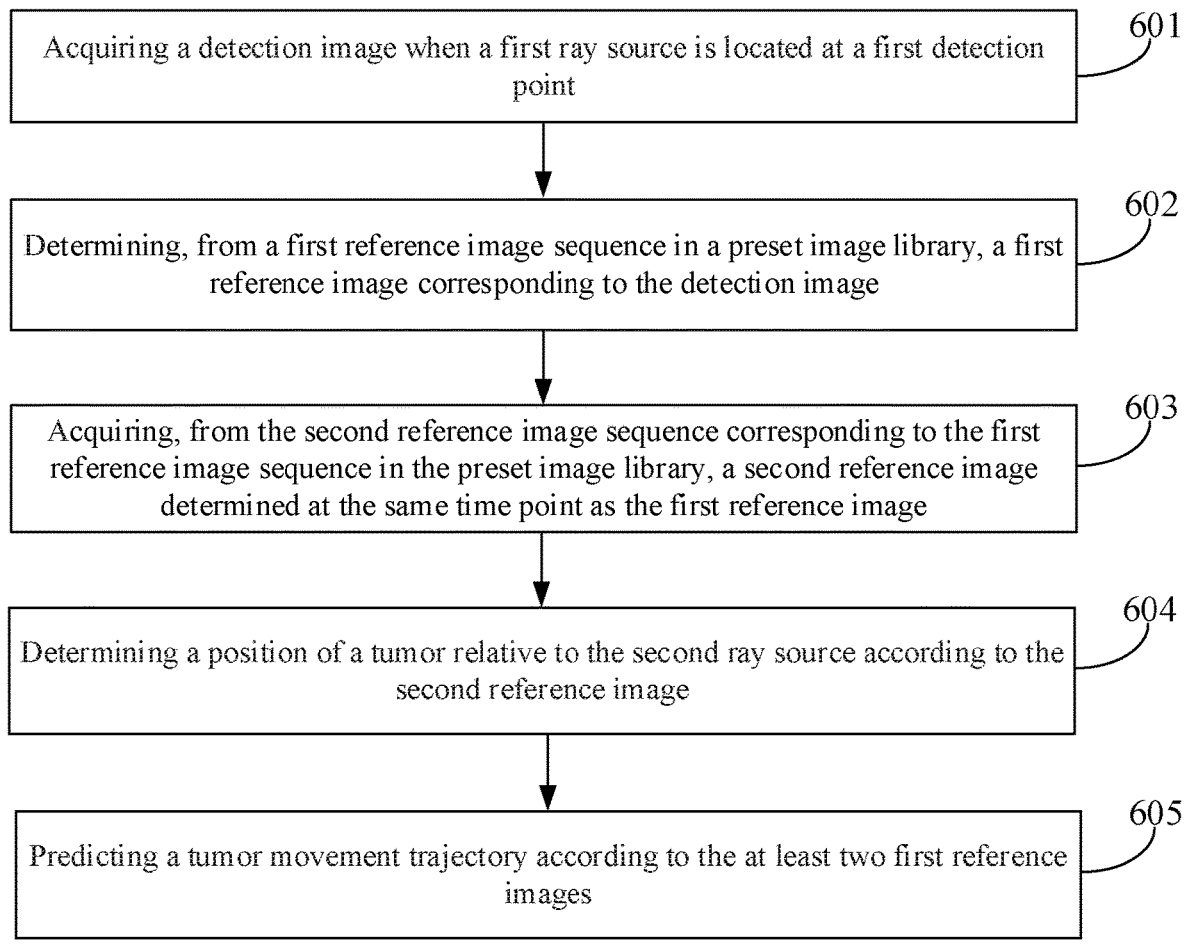
Figures 2, 6:
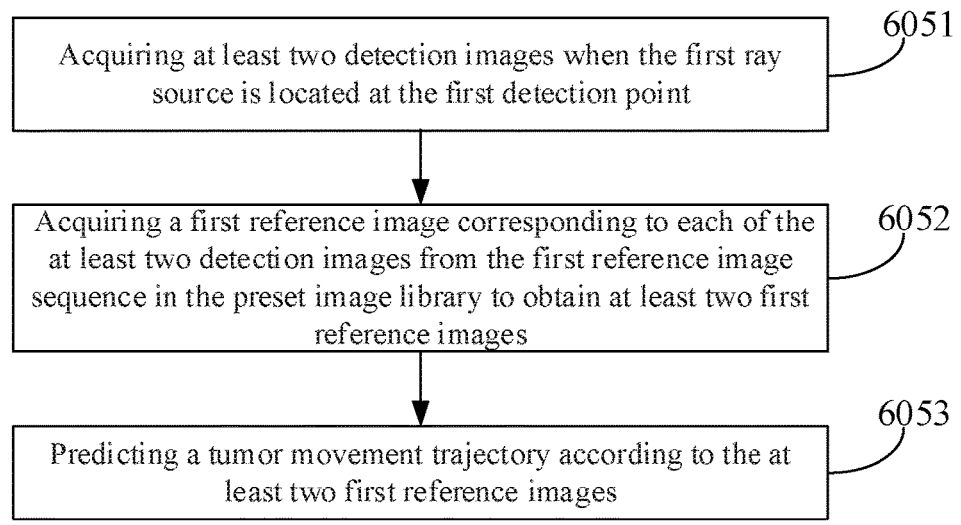

Another tumor tracking method provided by the present disclosure is described by taking the method shown in FIG. 2 as an example. FIG. 6-1 shows another implementation of the method provided by the present disclosure. As shown in FIG. 6-1, the method includes the following steps.

In step 601, a detection image when a first ray source is located at a first detection point is acquired. The detection image is an image determined when a radioactive ray, emitted by the first ray source at a first detection point toward a tumor area, is received by a detector.

In step 602, a first reference image corresponding to the detection image is determined from a first reference image sequence in a preset image library.

In step 603, a second reference image determined at the same time point as the first reference image is acquired from the second reference image sequence corresponding to the first reference image sequence in the preset image library.

In step 604, a position of a tumor relative to the second ray source is determined according to the second reference image.

In step 605, a tumor movement trajectory is predicted according to the at least two first reference images.

Steps 601 to 604 may refer to the specific description of the embodiment shown in FIG. 2, and are not repeated herein. In the embodiment of the present disclosure, the method further includes: acquiring at least two detection images when the first ray source is located at the first detection point; acquiring, from the first reference image sequence in the preset image library, a first reference image corresponding to each of the at least two detection images to obtain at least two first reference images; and predicting the tumor movement trajectory according to the at least two first reference images to track the tumor.

Exemplarily, FIG. 6-2 is a flowchart of a method for predicting a tumor movement trajectory provided by an embodiment of the present disclosure. Referring to FIG. 6-2, the method includes the following sub-steps.

In sub-step 6051, at least two detection images are acquired when the first ray source is located at the first detection point.

Each of the at least two detection images may be an image determined when the radioactive ray, emitted by the first ray source at the first detection point toward the tumor area, is received by the detector. In the embodiment of the present disclosure, the at least two detection images may be images determined when the radioactive rays, emitted by the first ray source at at least two first detection points toward the tumor area, are received by the detector; or, may be images determined when the radioactive rays, emitted by the first ray source at one first detection point toward the tumor area, are received by the detector. Thus, the sub-step 6051 may include: acquiring a detection image when the first ray source is located at each of the at least two first detection points to obtain at least two detection images; or acquiring at least two detection images when the first ray source is located at one first detection point.

In sub-step 6052, a first reference image corresponding to each of the at least two detection images is acquired from the first reference image sequence in the preset image library to obtain at least two first reference images.

When the at least two detection images in sub-step 6051 are images determined when the radioactive rays, emitted by the first ray source from at least two first detection points toward the tumor area, are received by the detector, in sub-step 6052, the tumor tracking device acquires the at least two first reference images from first reference image sequences in at least two reference image sequence groups in the preset image library.

When the at least two detection images in sub-step 6051 are images determined when the radioactive rays, emitted by the first ray source from one first detection point toward the tumor area, are received by the detector, in sub-step 6052, the tumor tracking device acquires the at least two first reference images from the first reference image sequence in one reference image sequence group in the preset image library This reference image sequence group is a reference image sequence group corresponding to a preset detection station in the preset image library. This first detection point is a first detection point in the preset detection station.

In sub-step 6053, a tumor movement trajectory is predicted according to the at least two first reference images.

Specifically, the tumor tracking device can determine a movement direction of the tumor according to images in the at least two first reference images, and can predict a first reference image at the next time point, a first reference image at a subsequent time point after the next time point, . . . , based on the at least two first reference images in combination with the preset image library, so as to obtain a series of first reference images. Then the tumor tracking device determines the tumor movement trajectory according to the images in the series of first reference images.

It should be noted that in the embodiment of the present disclosure, after the first reference image at each time point is predicted, the tumor tracking device may further determine the second reference image at each time point according to the first reference image at each time point, and determine the position of the tumor relative to the second ray source at each time point according to the image in the second reference image at each time point. A parameter of the second ray source can be adjusted according to the position of the tumor relative to the second ray source and the second ray source emits the radioactive ray toward the tumor based on the adjusted parameter. This is not repeated in the embodiment of the present disclosure.

Figures 1, 7:
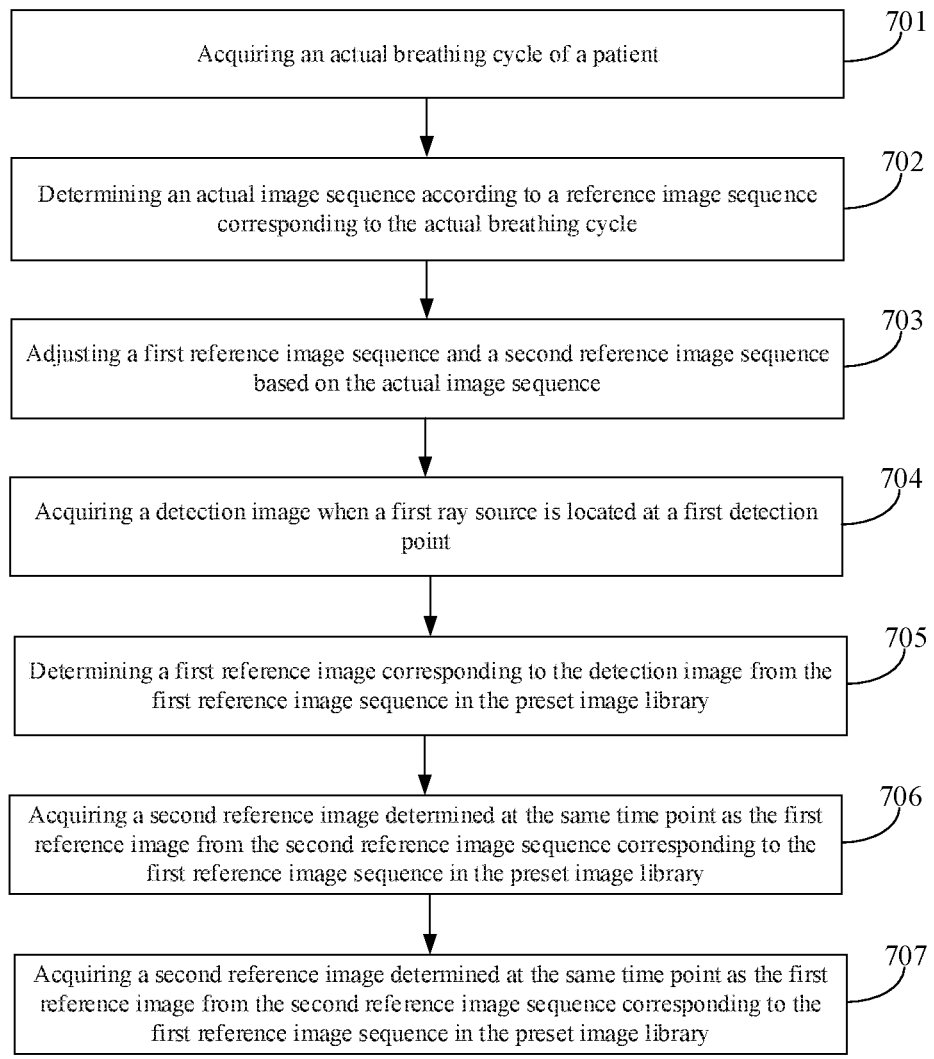
Figures 2, 7:
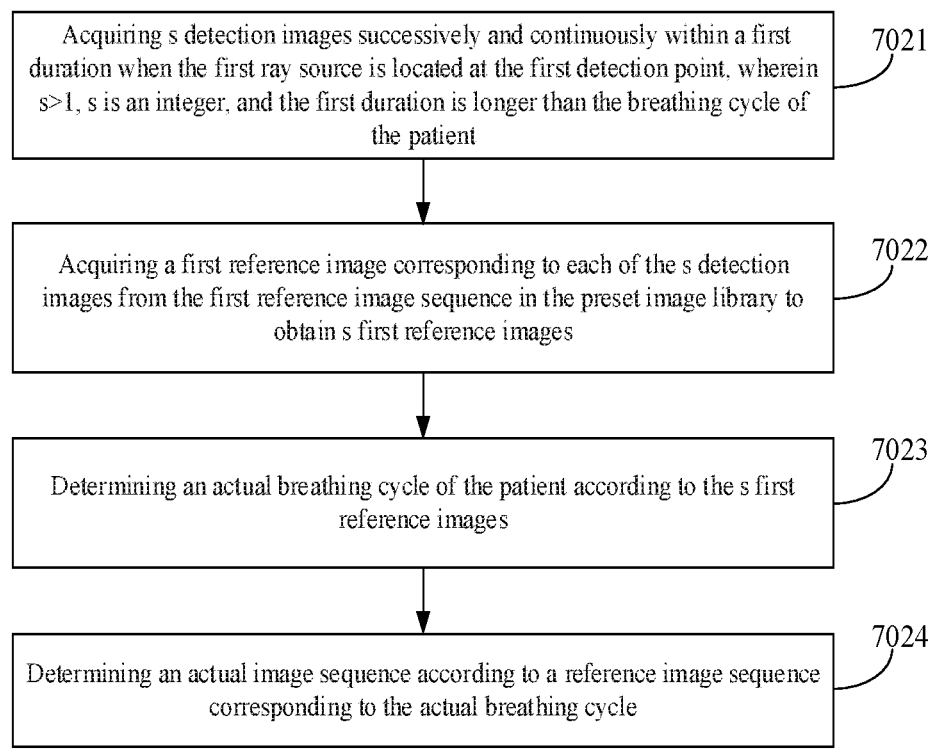

Another implementation provided by the present disclosure is described by taking the tracking method shown in FIG. 2 as an example. Referring to FIG. 7-1, the method includes the following steps.

In step 701, an actual breathing cycle of a patient is acquired.

In step 702 an actual image sequence is determined according to a reference image sequence corresponding to the actual breathing cycle.

In step 703, a first reference image sequence and a second reference image sequence are adjusted based on the actual image sequence.

Generally, the adjusted first reference image sequence may form a subset of the first reference image sequence in the preset image library, and the adjusted second reference image sequence may form a subset of the second reference image sequence in the preset image library. Therefore, by determining the first reference image according to the adjusted first reference image sequence and determining the second reference image according to the adjusted second reference image sequence, the complexity in determination of the first and second reference images can be reduced, and the efficiency is improved.

In step 704, a detection image when a first ray source is located at a first detection point is acquired. The detection image is an image determined when a radioactive ray, emitted by a first ray source at the first detection point toward a tumor area, is received by a detector.

In step 705, a first reference image corresponding to the detection image is determined from the first reference image sequence in the preset image library. The first reference image sequence in step 705 is the adjusted first reference image sequence in step 703.

In step 706, a second reference image determined at the same time point as the first reference image is acquired from the second reference image sequence corresponding to the first reference image sequence in the preset image library. The second reference image sequence in step 706 is the adjusted second reference image sequence in step 703.

In step 707, a position of a tumor relative to the second ray source is determined according to the second reference image.

In the embodiment of the present disclosure, the tumor tracking device can determine the actual breathing cycle of the patient, acquire the reference image sequence corresponding to the actual breathing cycle from the reference image sequence in the preset image library, determine the reference image sequence corresponding to the actual breathing cycle as the actual image sequence, adjust the first reference image sequence and the second reference image sequence according to the actual image sequence to obtain the adjusted first reference image sequence and the adjusted second reference image sequence, determine the first reference image and the second reference image according to the adjusted first and second reference image sequences, and determine the position of the tumor relative to the second ray source based on the determined second reference image. By determining the second reference image according to the adjusted second reference image sequence, the complexity in determination of the first and second reference images can be reduced, and the efficiency is improved.

Of course, this method is also applicable to other implementations in the present disclosure, and the above only takes the implementation shown in FIG. 2 as an example for illustration.

In the embodiment of the present disclosure, the specific implementation process of determining the actual image sequence according to the reference image sequence corresponding to the actual breathing cycle in step 702 may refer to FIG. 7-2 and related descriptions below, FIG. 7-2 is a flowchart of a method for determining an actual image sequence provided by an embodiment of the present disclosure. Referring to FIG. 7-2, the method includes the following sub-steps.

In sub-step 7021, s detection images are successively and continuously acquired within a first duration when the first ray source is located at the first detection point, wherein s>1, s is an integer, and the first duration is longer than the breathing cycle of the patient.

Each of the s detection images may be an image determined when the radioactive ray, emitted by the first ray source at the first detection point toward the tumor area, is received by the detector. In the embodiment of the present disclosure, the s detection images may be images determined when the radioactive rays, emitted by the first ray source at s first detection points toward the tumor area, are received by the detector, or may be images determined when the radioactive rays, emitted by the first ray source from one first detection point toward the tumor area, are received by the detector.

In sub-step 7022, a first reference image corresponding to each of the s detection images is acquired from the first reference image sequence in the preset image library to obtain s first reference images.

When the s detection images in sub-step 7021 are images determined when the radioactive rays, emitted by the first ray source from s first detection points toward the tumor area, are received by the detector, in sub-step 7022, the tumor tracking device acquires the s first reference images from first reference image sequences in s reference image sequence groups in the preset image library. When the s detection images in sub-step 7021 are images determined when the radioactive rays, emitted by the first ray source from one first detection point toward the tumor area, are received by the detector, in sub-step 7022, the tumor tracking device acquires the s first reference images from the first reference image sequence in one reference image sequence group in the preset image library. This reference image sequence group is a reference image sequence group corresponding to a preset detection station in the preset image library. This first detection point is a first detection point in the preset detection station.

In sub-step 7023, an actual breathing cycle of the patient is determined according to the s first reference images.

After acquiring the s first reference images, the tumor tracking device can determine an image of the tumor in each of the s first reference images, determine the positions of the tumor at each time point according to the images of the tumor, and determine the actual breathing cycle as double of a time difference between the determined time point of the reference image of a position when the tumor is the biggest and the determined time point of the reference image of a position when the tumor is the smallest.

In sub-step 7024, an actual image sequence is determined according to a reference image sequence corresponding to the actual breathing cycle.

After determining the actual breathing cycle, the tumor tracking device can determine the actual image sequence according to the reference image sequence corresponding to the actual breathing cycle.

It should be noted that in the embodiment of the present disclosure, after determining the s first reference images, the tumor tracking device can further determine the amplitude in regular movement of the tumor according to the s first reference images. Specifically, the tumor tracking device can determine the image of the tumor in each of the s first reference images, determine the maximum position of the tumor away from a midpoint (the midpoint of the regular movement) during the regular movement according to the images of the tumor, and determine the distance between a position point corresponding to the maximum position and the midpoint of the regular movement as the amplitude in the regular movement of the tumor, which is not repeated in the embodiment of the present disclosure.

It should also be noted that the order of the steps of the tumor tracking method provided by the embodiment of the present disclosure can be appropriately adjusted, and the steps can be correspondingly increased or decreased as needed. Varied methods which can be easily expected by any person skilled in the art within the technical scope disclosed by the present disclosure should be covered by the protection scope of the present disclosure, and thus are not repeated herein. In addition, in different implementations, each step can also be applied to other implementations. Another specific embodiment is provided below for illustration.

Figure 8:
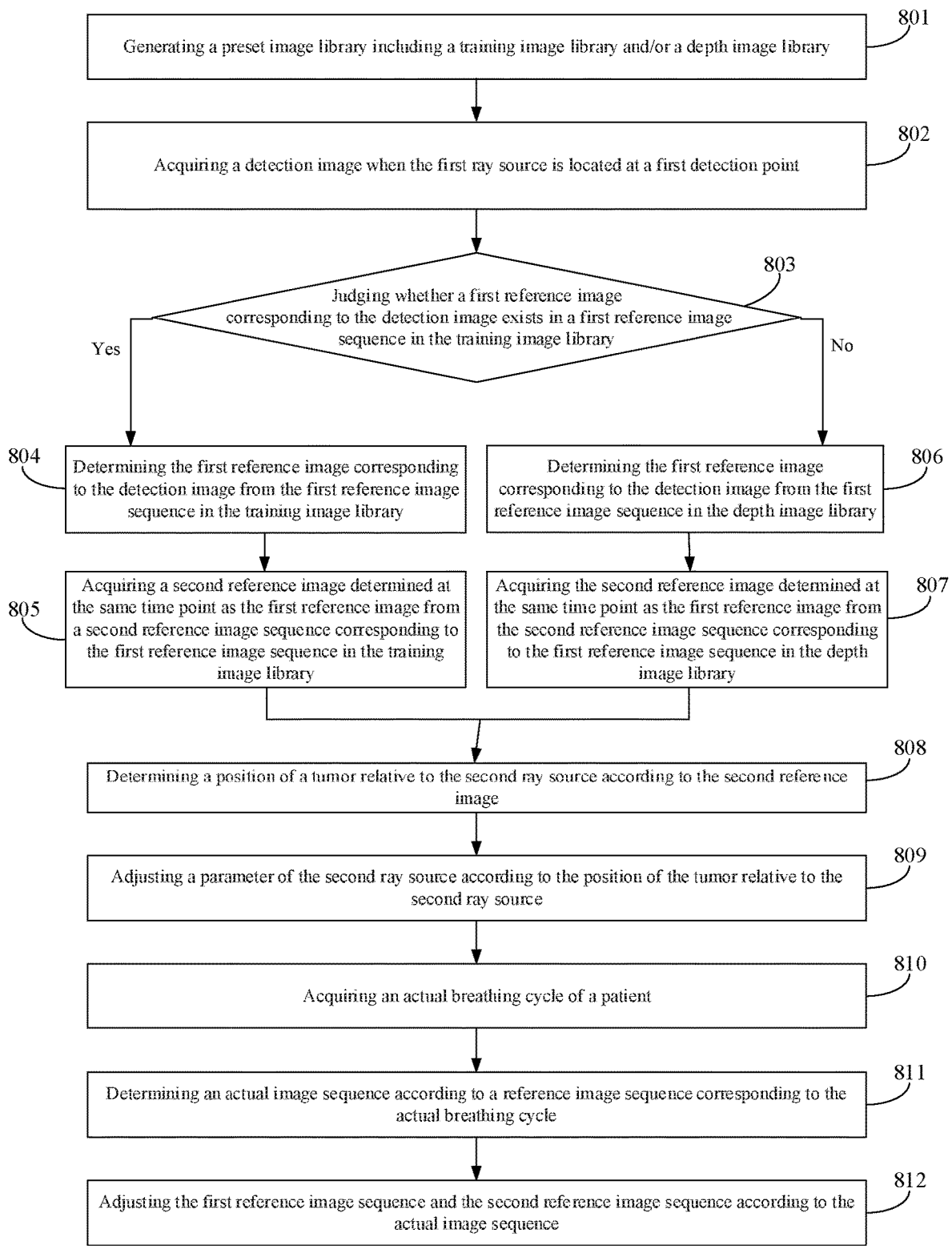
FIG. 8 is a flowchart of another tumor tracking method provided by an embodiment of the present disclosure.

As shown in FIG. 8, the present disclosure provides a tumor tracking method applied to radiation therapy equipment shown in FIG. 1. The radiation therapy equipment includes a first ray source and a second ray source, wherein the first ray source is an imaging source, and the second ray source is a treatment source. The method includes the following steps.

In step 801, a preset image library including a training image library and/or a depth image library is generated.

In step 802, a detection image when the first ray source is located at a first detection point is acquired. The detection image is an image determined when a radioactive ray, emitted by the first ray source at the first detection point toward a tumor area, is received by a detector.

In step 803, whether a first reference image corresponding to the detection image exists in a first reference image sequence in the training image library is judged.

In step 804, the first reference image corresponding to the detection image is determined from the first reference image sequence in the training image library.

In step 805, a second reference image determined at the same time point as the first reference image is acquired from a second reference image sequence corresponding to the first reference image sequence in the training image library.

In step 806, the first reference image corresponding to the detection image is determined from the first reference image sequence in the depth image library.

In step 807, the second reference image determined at the same time point as the first reference image is acquired from the second reference image sequence corresponding to the first reference image sequence in the depth image library.

In step 808, a position of a tumor relative to the second ray source is determined according to the second reference image.

In step 809, a parameter of the second ray source is adjusted according to the position of the tumor relative to the second ray source.

In step 810, an actual breathing cycle of a patient is acquired.

In step 811, an actual image sequence is determined according to a reference image sequence corresponding to the actual breathing cycle.

In step 812, the first reference image sequence and the second reference image sequence are adjusted according to the actual image sequence.

The above steps 801-812 are cyclically repeated till radioactive therapy of the tumor is completed. Specific implementations of the above steps may refer to other embodiments in the present disclosure, and are not repeated herein.

In summary, in the tumor tracking method provided by the embodiment of the present disclosure, after a detection image when the first ray source is located at the first detection point is acquired, by determining, from the first reference image sequence in the preset image library, a first reference image corresponding to the detection image and acquiring, from a second reference image sequence corresponding to the first reference image sequence in the preset image library, a second reference image determined at the same time point as the first reference image, the position of the tumor relative to the second ray source can be determined according to the second reference image. As such, the tumor tracking can be achieved by only using radiation therapy equipment and less hardware equipment is required. Thus, by providing the novel tumor tracking device, the problem of high cost in tumor tracking can be solved, which facilitates the reduction of the tumor tracking cost.

The following relates to a device provided by the embodiments of the present disclosure, and may be configured to execute the method provided by the embodiments of the present disclosure. Details not disclosed in the embodiments of the device provided by the present disclosure may refer to the embodiments of the method provided by the present disclosure.

Figures 1, 9:
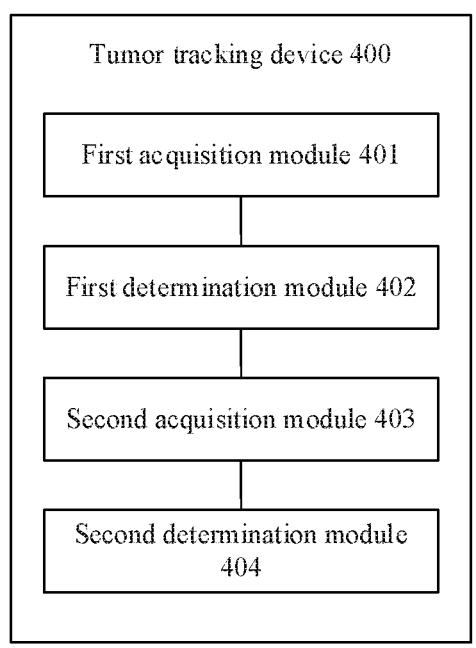
Figures 2, 9:
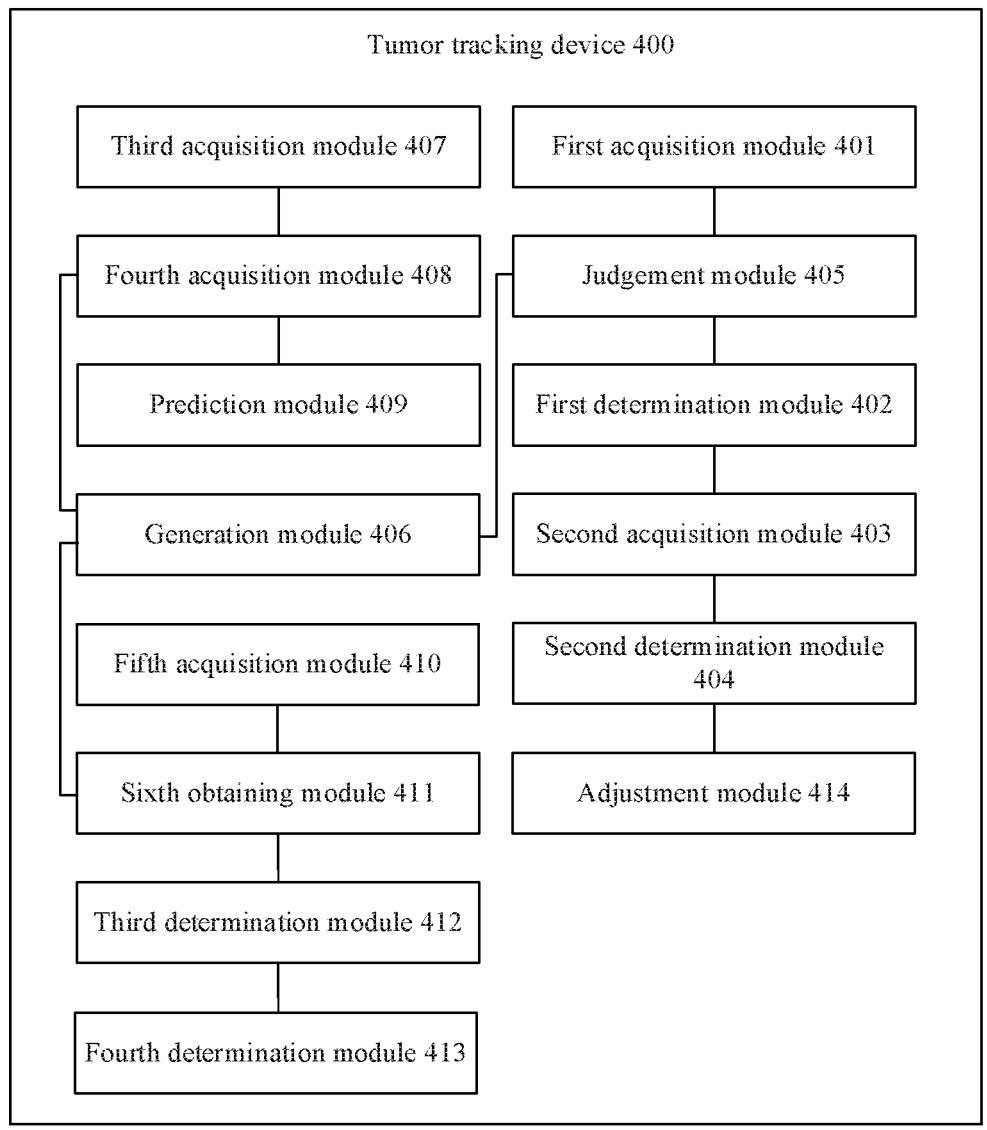

FIG. 9-1 is a block diagram of a tumor tracking device 400 provided by an embodiment of the present disclosure. The tumor tracking device 400 can be applied to radiation therapy equipment including a first ray source, a second ray source and a detector. When the first ray source is located at a first detection point, the second ray source is located at a second detection point, and the tumor tracking device 400 can be configured to execute any one of the methods provided in the embodiments shown in FIGS. 2 to 8. Referring to FIG. 9-1, the tumor tracking device 400 may include, but is not limited to the following modules.

A first acquisition module 401 is configured to acquire a detection image when the first ray source is located at the first detection point, wherein the detection image is an image determined when a radioactive ray, emitted by the first ray source at the first detection point to a tumor area, is received by the detector.

A first determination module 402 is configured to determine, from a first reference image sequence in a preset image library, a first reference image corresponding to the detection image. The preset image library includes the first reference image sequence and a second reference image sequence. The first reference image sequence is a reference image sequence determined based on an optical signal sent from a position of the first collection point toward the tumor area. The second reference image sequence is a reference image sequence determined based on an optical signal sent from a position of the second collection point toward the tumor area. The first detection point and the first collection point are at the same position relative to the tumor area. The second detection point and the second collection point are at the same position relative to the tumor area. Each of the first reference image sequence and the second reference image sequence includes a plurality of reference images determined at different time points.

A second acquisition module 403 is configured to acquire, from the second reference image sequence corresponding to the first reference image sequence in the preset image library, a second reference image determined at the same time point as the first reference image.

A second determination module 404 is configured to determine a position of a tumor relative to the second ray source according to the second reference image.

In summary, in the tumor tracking device provided by the embodiment of the present disclosure, after a detection image when the first ray source is located at the first detection point is acquired, by determining, from the first reference image sequence in the preset image library, a first reference image corresponding to the detection image and acquiring, from a second reference image sequence corresponding to the first reference image sequence in the preset image library, a second reference image determined at the same time point as the first reference image, the position of the tumor relative to the second ray source can be determined according to the second reference image. As such, the tumor tracking can be achieved by only using radiation therapy equipment and less hardware equipment is required. Thus, by providing the novel tumor tracking device, the problem of high cost in tumor tracking can be solved, which facilitates the reduction of the tumor tracking cost.

Exemplarily, the preset image library includes the training image library and/or the depth image library.

The reference image sequence(s) in the training image library is/are image sequence(s) determined when a patient is under breathing training. Each reference image sequence in the training image library includes n reference images determined at n different time points, n>1, and n is an integer.

The reference image sequence(s) in the depth image library is/are image sequence(s) determined when the patient is taking a deep breath. Each reference image sequence in the depth image library includes p reference images determined at p different time points, p>n, and p is an integer.

Exemplarily, the preset image library includes the training image library and the depth image library. FIG. 9-2 is a block diagram of another tumor tracking device 400 provided by an embodiment of the present disclosure. Referring to FIG. 9-2, the tumor tracking device 400 further includes the following modules on the basis of FIG. 9-1.

A judgement module 405 is configured to judge whether the first reference image exists in the first reference image sequence in the training image library.

When the first reference image exists in the first reference image sequence in the training image library, the first determination module 402 is configured to determine the first reference image from the first reference image sequence in the training image library, and the second acquisition module 403 is configured to acquire, from the second reference image sequence corresponding to the first reference image sequence in the training image library, a second reference image determined at the same time point as the first reference image.

Or, when the first reference image does not exist in the first reference image sequence in the training image library, the first determination module 402 is configured to determine the first reference image from the first reference image sequence in the depth image library, and the second acquisition module 403 is configured to acquire, from the second reference image sequence corresponding to the first reference image sequence in the depth image library, a second reference image determined at the same time point as the first reference image.

Further referring to FIG. 9-2, the tumor tracking device 400 further includes a generation module 406 configured to generate the preset image library.

Optionally, the generation module 406 is configured to determine the first collection point and the second collection point; send an optical signal from the position of the first collection point toward the tumor area, and determine the first reference image sequence based on the optical signal; and send an optical signal from the position of the second collection point toward the tumor area, and determine the second reference image sequence based on the optical signal. Or, the generation module 406 is configured to acquire a 4D image of the tumor area; and determine the first reference image sequence and the second reference image sequence according to the 4D image of the tumor area.

Optionally, the generation module 406 is configured to generate the depth image library and generate the training image library according to the depth image library.

Optionally, the preset image library includes a plurality of reference image sequence groups, each of which includes one first reference image sequence and one second reference image sequence.

The first ray source and the second ray source can rotate circumferentially around the tumor area. On one rotation circumference, the first ray source and the second ray source can be located at a plurality of preset detection stations, each of which includes one first detection point and one second detection point. Each of the preset detection stations corresponds to one of the reference image sequence groups.

Optionally, a central angle corresponding to an arc between the first detection point and the second detection point in each of the preset detection stations is equal to a central angle corresponding to an arc between the first detection points in any two adjacent preset detection stations. Or, the central angle corresponding to the arc between the first detection point and the second detection point in each preset detection station is equal to a central angle corresponding to an arc between the second detection points in any two adjacent preset detection stations Optionally, further referring to FIG. 9-2, the tumor tracking device 400 further includes the following modules.

A third acquisition module 407 is configured to acquire at least two detection images when the first ray source is located at the first detection point.

A fourth acquisition module 408 is configured to acquire, from the first reference image sequence in the preset image library, a first reference image corresponding to each of the at least two detection images to obtain at least two first reference images.

A prediction module 409 is configured to predict a tumor movement trajectory according to the at least two first reference images.

Optionally, the third acquisition module 407 is configured to obtain at least two detection images, each acquired when the first ray source is located at one of the at least two first detection points.

The fourth acquisition module 408 is configured to acquire, from first reference image sequences of at least two reference image sequence groups in the preset image library, at least two first reference images, wherein each first reference image is a reference image acquired from one first reference image sequence; the at least two reference image sequence groups are reference image sequence groups corresponding to at least two preset detection stations in the preset image library; and the at least two first detection points include each first detection point in each of the at least two preset detection stations. Or, the third acquisition module 407 is configured to acquire at least two detection images when the first ray source is located at one first detection point.

The fourth acquisition module 408 is configured to acquire at least two first reference images from the first reference image sequence in one reference image sequence group in the preset image library. This reference image sequence group is a reference image sequence group corresponding to a preset detection station in the preset image library. This first detection point is a first detection point in the preset detection station.

Optionally, further referring to FIG. 9-2, the tumor tracking device 400 further includes the following modules.

A fifth acquisition module 410 is configured to acquire, successively and continuously, s detection images within a first duration when the first ray source is located at the first detection point, wherein s>1, s is an integer, and the first duration is longer than a breathing cycle of the patient.

A sixth obtaining module 411 is configured to acquire, from the first reference image sequence in the preset image library, a first reference image corresponding to each of the s detection images to obtain s first reference images.

A third determination module 412 is configured to determine an actual breathing cycle of the patient according to the s first reference images.

A fourth determination module 413 is configured to determine an actual image sequence according to a reference image sequence corresponding to the actual breathing cycle.

Optionally, the fifth acquisition module 410 is configured to successively and continuously acquire s detection images within the first duration when the first ray source is located at each of the s first detection points.

The sixth acquisition module 411 is configured to acquire s first reference images from first reference image sequences of s reference image sequence groups in the preset image library, wherein each first reference image is a reference image acquired from one first reference image sequence; the s reference image sequence groups are reference image sequence groups corresponding to s preset detection stations in the preset image library; and the s first detection points include one first detection point in each of the s preset detection stations. Or, the fifth acquisition module 410 is configured to successively and continuously acquire s detection images within the first duration when the first ray source is located at one first detection point.

The sixth acquisition module 411 is configured to acquire s first reference images from the first reference image sequence in one reference image sequence group in the preset image library. This reference image sequence group is a reference image sequence group corresponding to a preset detection station in the preset image library. This first detection point is a first detection point in the preset detection station.

Optionally, further referring to FIG. 9-2, the tumor tracking device 400 further includes the following modules.

An adjustment module 414 is configured to adjust a parameter of the second ray source according to the position of the tumor relative to the second ray source.

Optionally, the first ray source is an imaging source; and the second ray source is a treatment source. The adjustment module 414 is configured to adjust at least one of a position parameter, a dose parameter and a radiation field parameter of the second ray source according to the position of the tumor relative to the second ray source.

In summary, in the tumor tracking device provided by the embodiment of the present disclosure, after a detection image when the first ray source is located at the first detection point is acquired, by determining, from the first reference image sequence in the preset image library, a first reference image corresponding to the detection image and acquiring, from a second reference image sequence corresponding to the first reference image sequence in the preset image library, a second reference image determined at the same time point as the first reference image, the position of the tumor relative to the second ray source can be determined according to the second reference image. As such, the tumor tracking can be achieved by only using radiation therapy equipment and less hardware equipment is required. Thus, by providing the novel tumor tracking device, the problem of high cost in tumor tracking can be solved, which facilitates the reduction of the tumor tracking cost.

Figure 10:
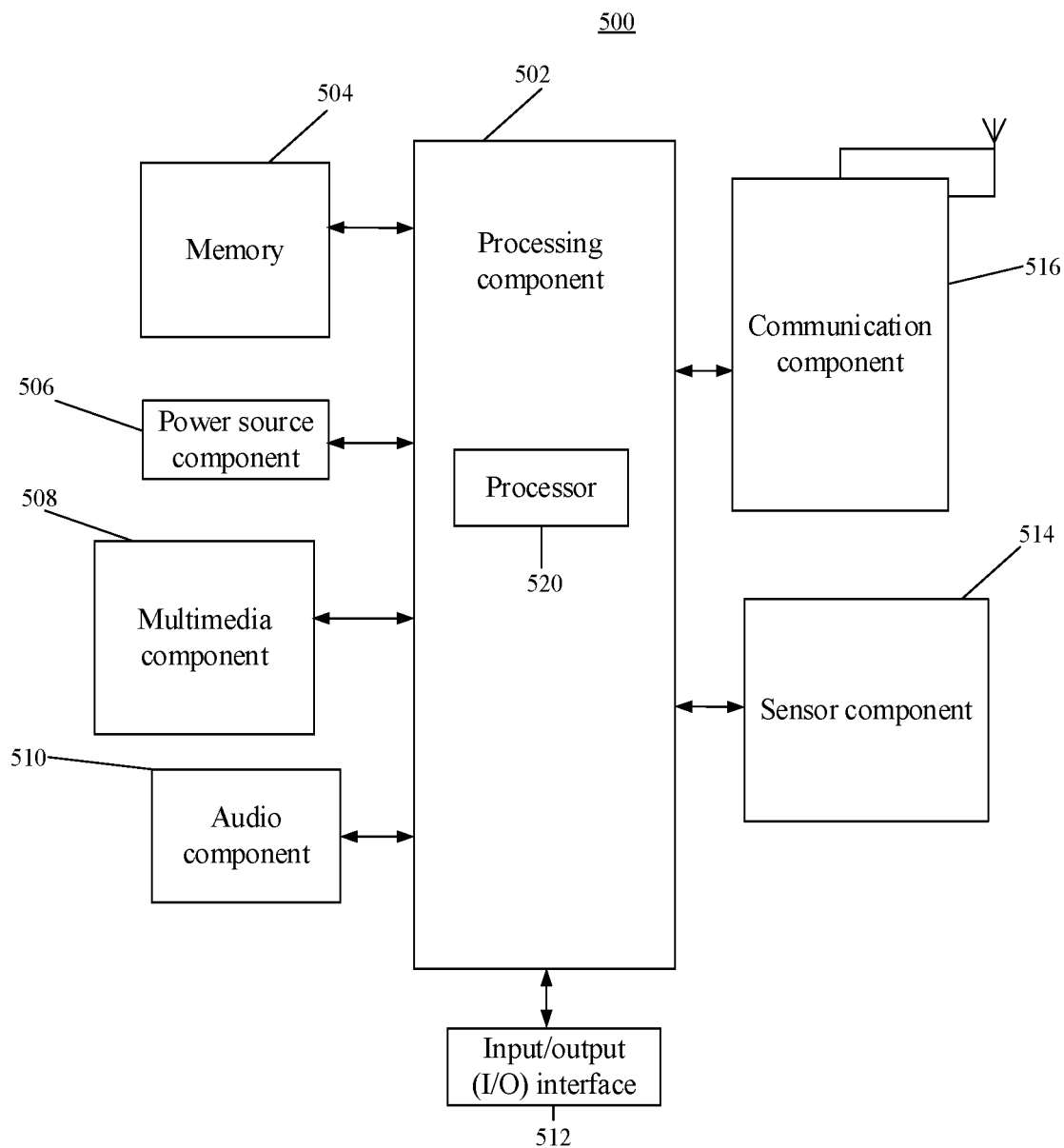
FIG. 10 is a schematic structural diagram of a terminal provided by an embodiment of the present disclosure.

FIG. 10 is a schematic structural diagram of a terminal 500 provided by an embodiment of the present disclosure. The terminal 500 may be medical equipment such as radiation therapy equipment, 3D CT equipment, 4D CT equipment, or the like.

Referring to FIG. 10, the terminal 500 may include one or more following components: a processing component 502, a memory 504, a power source component 506, a multimedia component 508, an audio component 510, an input/output (I/O) interface 512, a sensor component 514 and a communication component 516.

The processing component 502 typically controls overall operations of the terminal 500, such as the operations associated with display, data processing and recording. The memory 504 is configured to store various types of data to support the operations on the terminal 500. Examples of such data include instructions for any method operated on the terminal 500, image data, and the like. The power source component 506 provides power for various components of the terminal 500. The power source component 506 may include a power source management system, one or more power sources, and any other components associated with the generation, management, and distribution of power in the terminal 500. The multimedia component 508 includes a screen providing an output interface between the terminal 500 and a user.

The audio component 510 is configured to output and/or input audio signals. The I/O interface 512 provides an interface between the processing component 502 and peripheral interface modules, such as a keyboard, a click wheel, buttons, and the like. The sensor component 514 includes one or more sensors to provide the terminal 500 with status assessments of various aspects. The communication component 516 is configured to facilitate wired or wireless communication between the terminal 500 and other equipment.

In an exemplary embodiment, the terminal 500 may be implemented by one or more application specific integrated circuits (ASICs), digital signal processors (DSPs), digital signal processing devices (DSPDs), programmable logic devices (PLDs), field-programmable gate array (FPGAs), controllers, microcontrollers, microprocessors or other electronic components to execute the tumor tracking methods described above.

In an exemplary embodiment, there is also provided a non-transitory computer-readable storage medium including instructions, such as the memory 504 including the instructions which are executable by a processor 520 in the terminal 500 to execute the above tumor tracking methods. For example, the non-transitory computer-readable storage medium may be an ROM, a random access memory (RAM), a compact disc read-only memory (CD-ROM), a magnetic tape, a floppy disk, an optical data storage device, etc.

There is provided a non-transitory computer-readable storage medium. When instructions in the storage medium are executed by the processor in the terminal 500, the terminal 500 can be caused to execute the tumor tracking methods described above.

In summary, in the terminal provided by the embodiment of the present disclosure, after a detection image when the first ray source is located at the first detection point is acquired, by determining, from the first reference image sequence in the preset image library, a first reference image corresponding to the detection image and acquiring, from a second reference image sequence corresponding to the first reference image sequence in the preset image library, a second reference image determined at the same time point as the first reference image, the position of the tumor relative to the second ray source can be determined according to the second reference image. As such, the tumor tracking can be achieved by only using radiation therapy equipment and less hardware equipment is required. Thus, by providing the novel tumor tracking device, the problem of high cost in tumor tracking can be solved, which facilitates the reduction of the tumor tracking cost.

There is provided a readable storage medium. Instructions are stored in the readable storage medium. When the readable storage medium runs on a processing component, the processing component is caused to execute any one of the methods described in FIGS. 2 to 8.

There is provided a computer program product including instructions. When the computer program product runs on a computer, the computer is caused to execute any one of the methods described in FIGS. 2 to 8.

The term "and/or" in the present disclosure is merely configured to describe association relations among associated objects, and may indicate three relationships. For example, "A and/or B" may indicate that A exists alone, or A and B exist simultaneously, or B exists alone. In addition, the character "/" generally indicates that the objects in the context are in an "OR" relationship.

The serial numbers of the embodiments of the present disclosure are merely for purpose of description, and do not represent the preference of the embodiments.

Persons of ordinary skill in the art can understand that all or part of the steps described in the above embodiments can be completed through hardware, or through relevant hardware instructed by applications stored in a computer readable storage medium, such as a read-only memory, a disk or a CD, etc.

The foregoing descriptions are merely preferred embodiments of the present disclosure, and are not intended to limit the present disclosure. Within the spirit and principles of the present disclosure, any modifications, equivalent substitutions, improvements, etc., are within the protection scope of the present disclosure.

The invention claimed is:

1. A tumor tracking method applied to radiation therapy equipment, wherein the radiation therapy equipment comprises a first ray source, a second ray source and a detector; when the first ray source is located at a first detection point, the second ray source is located at a second detection point, the method comprising:
    acquiring a detection image when the first ray source is located at the first detection point, wherein the detection image is an image determined when a radioactive ray, emitted by the first ray source at the first detection point toward a tumor area, is received by the detector;
    determining, from a first reference image sequence in a preset image library, a first reference image corresponding to the detection image, wherein the preset image library comprises the first reference image sequence and a second reference image sequence, the first reference image sequence is a reference image sequence determined based on an optical signal sent from a position of a first collection point toward the tumor area, the second reference image sequence is a reference image sequence determined based on an optical signal sent from a position of a second collection point toward the tumor area, the first detection point and the first collection point are at the same position relative to the tumor area, the second detection point and the second collection point are at the same position relative to the tumor area, and each of the first and second reference image sequences comprises a plurality of reference images determined at different time points;

acquiring, from the second reference image sequence corresponding to the first reference image sequence in the preset image library, a second reference image determined at the same time point as the first reference image; and determining a position of a tumor relative to the second ray source according to the second reference image.

2. The method of claim 1, wherein the preset image library comprises a training image library and/or a depth image library;

reference image sequences in the training image library are image sequences determined when a patient is under breathing training, each reference image sequence in the training image library comprises n reference images determined at n different time points, n>1, and n is an integer; and reference image sequences in the depth image library are image sequences determined when the patient is taking a deep breath, each reference image sequence in the depth image library comprises p reference images determined at p different time points, p>n, and p is an integer.

3. The method of claim 2, wherein the preset image library comprises the training image library and the depth image library;

prior to determining, from the first reference image sequence in the preset image library, the first reference image corresponding to the detection image, the method further comprises:

determining whether the first reference image exists in the first reference image sequence in the training image library;

in response to determining that the first reference image exists in the first reference image sequence in the training image library:

the determining, from the first reference image sequence in the preset image library, the first reference image corresponding to the detection image comprises: determining the first reference image from the first reference image sequence in the training image library, and the acquiring, from the second reference image sequence corresponding to the first reference image sequence in the preset image library, the second reference image determined at the same time point as the first reference image comprises: acquiring, from the second reference image sequence corresponding to the first reference image sequence in the training image library, the second reference image determined at the same time point as the first reference image;

or, in response to determining that the first reference image does not exist in the first reference image sequence of the training image library:

the determining, from the first reference image sequence in the preset image library, the first reference image corresponding to the detection image comprises: determining the first reference image from the first reference image sequence in the depth image library, and the acquiring, from the second reference image sequence corresponding to the first reference image sequence in the preset image library, the second reference image determined at the same time point as the first reference image comprises: acquiring, from the second reference image sequence corresponding to the first reference image sequence in the depth image library, the second reference image determined at the same time point as the first reference image.

4. The method of claim 1, wherein prior to determining, from the first reference image sequence in the preset image library, the first reference image corresponding to the detection image, the method further comprises: generating the preset image library.

5. The method of claim 4, wherein
the generating the preset image library comprises:
determining the first collection point and the second collection point,
sending the optical signal from the position of the first collection point toward the tumor area, and determining the first reference image sequence based on the optical signal, and
sending the optical signal from the position of the second collection point toward the tumor area, and determining the second reference image sequence based on the optical signal;

or, the generating the preset image library comprises:
acquiring a 4D image of the tumor area, and
determining the first reference image sequence and the second reference image sequence according to the 4D image of the tumor area.

6. The method of claim 4, wherein the generating the preset image library comprises:
generating the depth image library; and
generating the training image library according to the depth image library.

7. The method of claim 1, wherein
the preset image library comprises a plurality of reference image sequence groups, and each of the reference image sequence groups comprises one first reference image sequence and one second reference image sequence;

the first ray source and the second ray source are capable of rotating circumferentially around the tumor area; on one rotation circumference, the first ray source and the second ray source are capable of being located at a plurality of preset detection stations; and each of the preset detection stations comprises one first detection point and one second detection point, and each of the preset detection stations corresponds to one of the reference image sequence groups.

8. The method of claim 7, wherein
a central angle corresponding to an arc between the first detection point and the second detection point in each of the preset detection stations is equal to a central angle corresponding to an arc between the first detection points in any two adjacent preset detection stations; or, the central angle corresponding to the arc between the first detection point and the second detection point in each of the preset detection stations is equal to a central angle corresponding to an arc between the second detection points in any two adjacent preset detection stations.

9. The method of claim 8, further comprising:
acquiring at least two detection images when the first ray source is located at the first detection point;
acquiring, from the first reference image sequence in the preset image library, a first reference image corresponding to each of the at least two detection images to obtain at least two first reference images; and
predicting a tumor movement trajectory according to the at least two first reference images.

10. The method of claim 8, further comprising:
acquiring, successively and continuously, s detection images within a first duration when the first ray source is located at the first detection point, wherein s>1, s is an integer, and the first duration is longer than a breathing cycle of the patient;
acquiring, from the first reference image sequence in the preset image library, a first reference image corresponding to each of the s detection images to obtain s first reference images;
determining an actual breathing cycle of the patient according to the s first reference images; and
determining an actual image sequence according to a reference image sequence corresponding to the actual breathing cycle.

11. The method of claim 1, wherein after determining the position of the tumor relative to the second ray source according to the second reference image, the method further comprises:
adjusting a parameter of the second ray source according to the position of the tumor relative to the second ray source.

12. The method of claim 11, wherein the first ray source is an imaging source, the second ray source is a treatment source, and the adjusting the parameter of the second ray source according to the position of the tumor relative to the second ray source comprises:
adjusting at least one of a position parameter, a dose parameter and a radiation field parameter of the second ray source according to the position of the tumor relative to the second ray source.

13. A tumor tracking device applied to radiation therapy equipment, wherein the radiation therapy equipment comprises a first ray source, a second ray source and a detector, the device comprising:
a first acquisition module, configured to acquire a detection image when the first ray source is located at the first detection point, wherein the detection image is an image determined when a radioactive ray, emitted by the first ray source at the first detection point toward a tumor area, is received by the detector;
a first determination module, configured to determine, from a first reference image sequence in a preset image library, a first reference image corresponding to the detection image, wherein the preset image library comprises the first reference image sequence and a second reference image sequence, the first reference image sequence is a reference image sequence determined based on an optical signal sent from a position of a first collection point toward the tumor area, the second reference image sequence is a reference image sequence determined based on an optical signal sent from a position of a second collection point toward the tumor area, the first detection point and the first collection point are at the same position relative to the tumor area, a second detection point at which the second ray source is located and the second collection point are at the same position relative to the tumor area, and each of the first and second reference image sequences comprises a plurality of reference images determined at different time points;
a second acquisition module, configured to acquire, from the second reference image sequence corresponding to the first reference image sequence in the preset image library, a second reference image determined at the same time point as the first reference image; and
a second determination module, configured to determine a position of a tumor relative to the second ray source according to the second reference image.

14. The device of claim 13, wherein the preset image library comprises a training image library and/or a depth image library;
reference image sequences in the training image library are image sequences determined when a patient is under breathing training, each reference image sequence in the training image library comprises n reference images determined at n different time points, n>1, and n is an integer; and
reference image sequences in the depth image library are image sequences determined when the patient is taking a deep breath, each reference image sequence in the depth image library comprises p reference images determined at p different time points, p>n, and p is an integer.

15. The device of claim 14, wherein the preset image library comprises the training image library and the depth image library; and the device further comprises:
a judgement module, configured to determine whether the first reference image exists in the first reference image sequence in the training image library;
in response to the judgment module determining that the first reference image exists in the first reference image sequence in the training image library:
the first determination module is configured to determine the first reference image from the first reference image sequence in the training image library, and
the second acquisition module is configured to acquire, from the second reference image sequence corresponding to the first reference image sequence in the training image library, the second reference image determined at the same time point as the first reference image;
or,
in response to the judgment module determining that the first reference image does not exist in the first reference image sequence of the training image library:
the first determination module is configured to determine the first reference image from the first reference image sequence in the depth image library, and
the second acquisition module is configured to acquire, from the second reference image sequence corresponding to the first reference image sequence in the depth image library, the second reference image determined at the same time point as the first reference image.

16. The device of claim 13, further comprising a generation module configured to generate the preset image library.

17. The device of claim 13, further comprising:
- a third acquisition module, configured to acquire at least two detection images when the first ray source is located at the first detection point;
- a fourth acquisition module, configured to acquire, from the first reference image sequence in the preset image library, a first reference image corresponding to each of the at least two detection images to obtain at least two first reference images; and
- a prediction module, configured to predict a tumor movement trajectory according to the at least two first reference images.

18. The device of claim 13, further comprising:
- a fifth acquisition module, configured to acquire, successively and continuously, s detection images within a first duration when the first ray source is located at the first detection point, wherein s>1, s is an integer, and the first duration is longer than a breathing cycle of a patient;
- a sixth acquisition module, configured to acquire, from the first reference image sequence in the preset image library, a first reference image corresponding to each of the s detection images to obtain s first reference images;
- a third determination module, configured to determine an actual breathing cycle of the patient according to the s first reference images; and
- a fourth determination module, configured to determine an actual image sequence according to a reference image sequence corresponding to the actual breathing cycle.

19. The device of claim 13, further comprising an adjustment module configured to adjust a parameter of the second ray source according to the position of the tumor relative to the second ray source.

20. A non-transitory computer readable storage medium storing instructions that, when executed by a processor, cause the processor to execute a tumor tracking method applied to radiation therapy equipment comprising a first ray source, a second ray source, and a detector, the method comprising:
- acquiring a detection image when the first ray source is located at a first detection point, wherein the detection image is an image determined when a radioactive ray, emitted by the first ray source at the first detection point toward a tumor area, is received by the detector;
- determining, from a first reference image sequence in a preset image library, a first reference image corresponding to the detection image, wherein the preset image library comprises the first reference image sequence and a second reference image sequence, the first reference image sequence is a reference image sequence determined based on an optical signal sent from a position of a first collection point toward the tumor area, the second reference image sequence is a reference image sequence determined based on an optical signal sent from a position of a second collection point toward the tumor area, the first detection point and the first collection point are at the same position relative to the tumor area, a second detection point at which the second ray source is located and the second collection point are at the same position relative to the tumor area, and each of the first and second reference image sequences comprises a plurality of reference images determined at different time points;
- acquiring, from the second reference image sequence corresponding to the first reference image sequence in the preset image library, a second reference image determined at the same time point as the first reference image; and
- determining a position of a tumor relative to the second ray source according to the second reference image.

* * * * *